(12) United States Patent
Lauks et al.

(10) Patent No.: US 7,094,330 B2
(45) Date of Patent: Aug. 22, 2006

(54) HETEROGENEOUS MEMBRANE ELECTRODES

(75) Inventors: Imants Lauks, Ottawa (CA); Andrzej Maczuszenko, Etobicoke (CA)

(73) Assignee: Epocal Inc., Ottawa (CA)

( * ) Notice: Subject to any disclaimer, the term of this patent is extended or adjusted under 35 U.S.C. 154(b) by 530 days.

(21) Appl. No.: 10/307,481

(22) Filed: Dec. 2, 2002

(65) Prior Publication Data

US 2006/0137980 A1 Jun. 29, 2006

(51) Int. Cl.
*G01N 27/403* (2006.01)

(52) U.S. Cl. ...................... 205/775; 204/435

(58) Field of Classification Search ........... 204/403.02, 204/403.05, 435; 210/500.27–500.32, 500.42; 205/775
See application file for complete search history.

(56) References Cited

U.S. PATENT DOCUMENTS

| | | | |
|---|---|---|---|
| 4,062,750 A | 12/1977 | Butler | |
| 4,133,735 A | 1/1979 | Afromowitz et al. | |
| 4,225,410 A | 9/1980 | Pace | |
| 4,276,141 A | 6/1981 | Hawkins | |
| 4,342,964 A | 8/1982 | Diamond et al. | |
| 4,431,508 A | 2/1984 | Brown, Jr. et al. | |
| 4,592,824 A | 6/1986 | Smith et al. | |
| 4,613,422 A * | 9/1986 | Lauks ........................ | 204/419 |
| 4,682,602 A | 7/1987 | Prohaska | |
| 4,689,309 A | 8/1987 | Jones | |
| 4,877,528 A * | 10/1989 | Friesen et al. ......... | 210/500.29 |
| 4,933,048 A | 6/1990 | Lauks | |
| 5,030,310 A * | 7/1991 | Wogoman .................. | 156/252 |
| 5,063,081 A | 11/1991 | Cozzette et al. | |
| 5,078,854 A | 1/1992 | Burgess et al. | |
| 5,183,549 A | 2/1993 | Joseph et al. | |
| 5,200,051 A | 4/1993 | Cozzette et al. | |
| 5,385,659 A | 1/1995 | Gumbrecht et al. | |
| 5,445,920 A | 8/1995 | Saito | |
| 5,496,521 A | 3/1996 | Leiner | |
| 5,514,253 A | 5/1996 | Davis et al. | |
| 5,554,272 A | 9/1996 | Benco et al. | |
| 5,658,444 A | 8/1997 | Black et al. | |
| 5,708,247 A | 1/1998 | McAleer et al. | |
| 5,727,548 A | 3/1998 | Hill et al. | |
| 6,432,296 B1 | 8/2002 | Daniel et al. | |
| 6,484,045 B1 * | 11/2002 | Holker et al. .............. | 600/345 |
| 6,766,817 B1 | 7/2004 | da Silva | |

FOREIGN PATENT DOCUMENTS

EP 0 325 562 7/1989

(Continued)

OTHER PUBLICATIONS

Matysik et al, "A Disposable Electrode Based on Zeolite-Polymer Membranes for Potentiometric Titrations of Ionic Surfactants", *Sens Actuators, B. Chem; Sensors and Actuators, B: Chemical*, Jun. 20, 2002, vol. 85, No. 1-2, pp. 104-108, XP002271483.

*Primary Examiner*—Alex Noguerola
(74) *Attorney, Agent, or Firm*—Borden Ladner Gervais LLP

(57) ABSTRACT

The present invention relates to planar electrochemical sensors with membrane coatings used to perform chemical analyses. The object of this invention is to provide unit-use disposable sensors of very simple and economical construction, preferably with only a single membrane coating on an electrode. The invented devices are potentiometric salt-bridge reference electrodes constructed with a heterogeneous membrane coating of a conductor. The heterogeneous membrane is a formulation that concurrently supports non-volatile species transport through an electrolyte compartment and gas transport through a hydrophobic compartment.

43 Claims, 9 Drawing Sheets

FOREIGN PATENT DOCUMENTS

| | | |
|---|---|---|
| EP | 0 551 769 | 7/1993 |
| EP | 1 087 225 | 3/2001 |
| EP | 1 193 495 | 4/2002 |
| GB | 1 584 788 | 2/1981 |
| RO | 81891 A * | 5/1983 |
| WO | WO 00/58720 | 10/2000 |

* cited by examiner

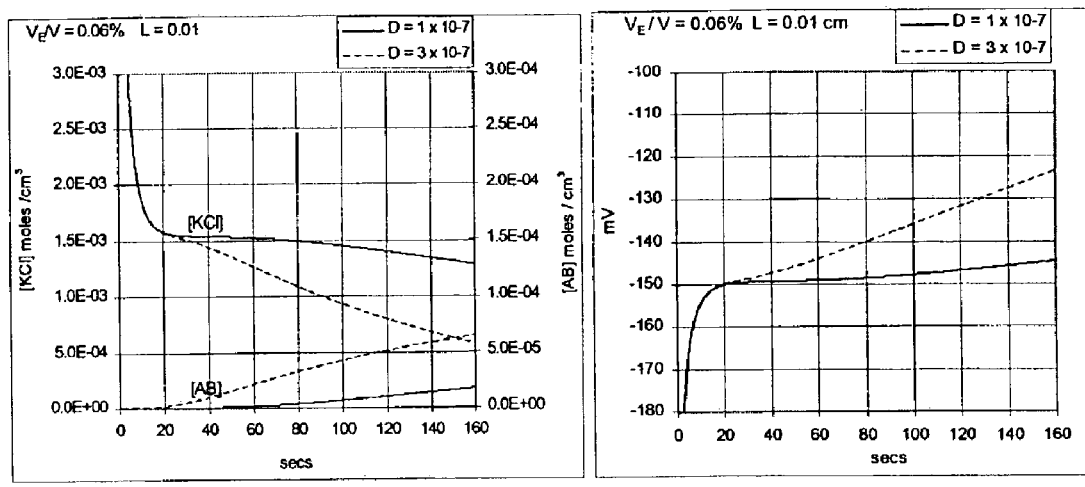
FIG. 5A                    FIG. 5B

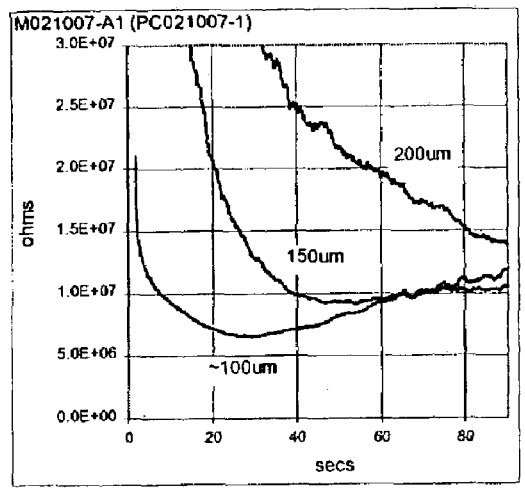 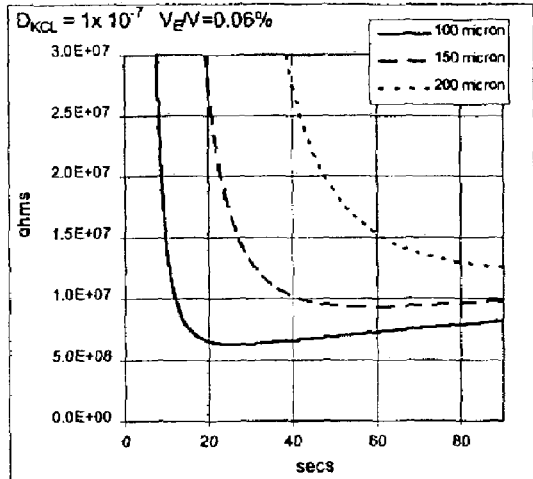
FIG. 6A                FIG. 6B
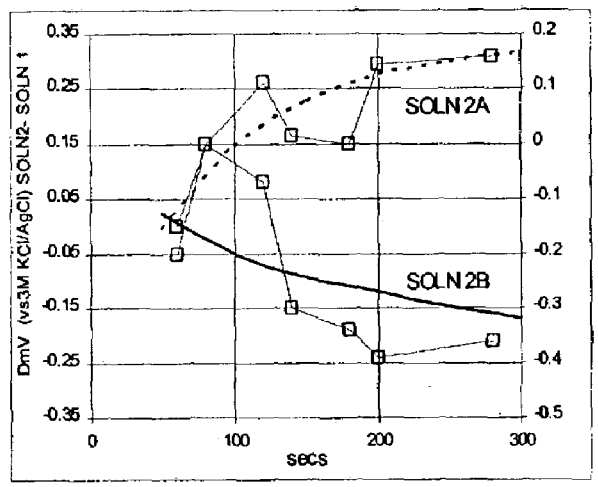
FIG. 7

HETEROGENEOUS MEMBRANE ELECTRODES

FIELD OF INVENTION

The invention relates to electrochemical sensors for the analysis of aqueous solutions. In particular, the invention relates to the construction of unit-use reference electrodes for such sensors.

BACKGROUND OF THE INVENTION

Prior-art electrochemical sensors typically consist of an electrochemical cell with two, sometimes three electrodes. The first electrode is responsive to a chemical species in the test solution and is called the indicator electrode. The second electrode called the reference electrode is typically non-responsive to changes in the composition of the test solution. In polarography a third, current-injecting counter electrode is sometimes used.

As is appreciated by those in the art, the performance of an electrochemical sensor as part of a chemistry analyzer for quantitative measurement of chemicals in aqueous solutions is determined by its dose-response curve. For a linear sensor this can be uniquely determined by two coefficients: a slope and an intercept. For a dose-response curve that is non-linear, three or more coefficients may be required. As is also known in the art, a sensor's coefficients vary over time if it is used more than once. The coefficients also vary to some extent from sensor to sensor because no two sensors can be manufactured identically. Therefore, a calibration is generally required to uniquely determine a sensor's dose-response curve. In an automated chemistry analyzer the calibration is provided by fluidic elements (calibration fluids, pumps, valves, conduits etc.) contained within the analyzer. If a sensor is deployed as a reusable device, the chemistry analyzer's calibration fluidics often provides for at least two calibration points and a wash solution. This is because the slope and intercept of the dose-response curve can change through repeated uses. For a unit-use device no calibration would be required if the slope and intercept were sufficiently reproducible from sensor to sensor during manufacture and storage. A single calibrator would be required if either one of the coefficients was reproducible, the other not, and two calibrators if neither coefficient was reproducible (more calibrators could be required for devices with non-linear dose-response curves).

Often the goal of a manufacturer of chemistry analyzers is to produce sensors sufficiently cheaply so that they can be deployed as unit-use devices, thus eliminating or simplifying the chemistry analyzer's often very complex fluidics required for the washing and calibrating of multiple-use sensors. To this end, manufacturers have investigated planar technologies for low cost sensor manufacture. Such planar technologies also purport to provide appropriate control of the materials of construction and manufacturing processes to achieve device-to-device reproducibility in high volume production.

Sensors made by planar technology have included both thick-film and thin-film micro-fabrication technologies. Thick film processed devices such as plastic diagnostic strips are disclosed in U.S. Pat. No. 5,727,548 for example. Devices made by planar technology also include thick film processed planar substrates as in hybrid circuit or printed circuit manufacture. U.S. Pat. Nos. 4,133,735, 4,225,410 for example disclose devices with electrodes made by thick film fabrication processes such as plating, screen-printing, dispensing and the like.

Micro-fabrication technology with its proven superior dimensional control also has been used to make devices for unit-use applications. Micro-fabrication technology employs wafer-level processes such as photolithography on silicon wafers. U.S. Pat. Nos. 4,062,750 4,933,048 and 5,063,081 disclose devices containing electrodes made by thin-film micro-fabrication processes on silicon substrates.

Regardless of which of the above variants of planar technology is being used, planar devices of the prior art have been complex to manufacture and are therefore still relatively expensive.

To better appreciate the complexity of prior-art planar sensors, consider their typical components of construction. A planar electrochemical sensor of the prior art is a device consisting of one or more metal conductor elements on a planar insulating substrate. One region of the metal conductor element is provided for connection to an external measuring circuit. A planar electrode is formed in another region of the metal conductor element. The planar electrode of such a prior-art electrochemical sensor consists typically of one or more additional metal layers and metal salt over-layers over-coating the metal conductor element. Planar electrodes are typically then coated with several additional functional layers as outlined below.

The planar electrode of the planar sensor is typically coated by an integral electrolyte medium. This integral electrolyte may be a liquid aqueous solution or, more commonly, a solid hydrophilic layer such as a gel material that acts like an aqueous electrolyte. In use of the planar sensor, the planar electrode region and its integral electrolyte over-layer is immersed in an aqueous solution to be tested. Chemical species from the test solution permeate into the integral electrolyte layer, dissolve and often react with other reagents contained within the integral electrolyte layer. Components of the integral electrolyte layer undergo electrochemical reaction at the electrode surface generating a current or a voltage. When the measured current or voltage of the sensor is selectively proportional to the concentration of a species in the test solution that is transported from the test solution into the sensor there is the basis for an indicator electrode for that species. If the voltage is independent of test solution composition there is the basis for a reference electrode. In prior-art electrochemical sensors it is generally required that chemical reagents within the integral electrolyte layer be at constant concentrations during the time of the measurement.

It is generally required that chemicals contained within the test solution that are deleterious to the sensor reactions be rejected from the integral electrolyte layer. As is known in the art such contaminants may affect chemical reactions within the integral electrolyte layer, or they may themselves be electro-active and cause a voltage or current that interferes with the measured voltage or current due to the species being analyzed. Retention of reagent chemical and rejection of contaminants is often achieved by interposing one or more materials between the integral electrolyte and the test solution. Transport of the sensed species from the test solution into the integral electrolyte layer takes place through the interposed materials by diffusion or through holes or pores in those materials. In many cases of prior-art planar sensors it is also necessary to interpose an additional semi-permeable layer between the electrode and the integral electrolyte layer. The purpose of this electrode-modifying layer is to allow transport of the chemicals of the sensor reaction while rejecting electroactive interferents or species that poison the electrode.

In summary, as described above, planar electrochemical sensors of the prior art including prior-art reference electrodes generally consist of numerous elements. The resulting devices are complex to manufacture and relatively costly. To further illustrate their complexity, the devices of the prior art addressed by the current invention are described in more detail in the following section.

Potentiometric Salt-Bridge Reference Electrode Prior Art

Salt-bridge reference electrodes of the prior art consists of an electrode, usually silver—silver chloride contacted by an integral reservoir of a concentrated aqueous solution of a salt with equi-mobile ions, typically potassium chloride. The integral aqueous electrolyte reservoir is called the salt bridge. The electrolyte reservoir contacts the test solution at a constrained-flow liquid junction. An ideal salt-bridge reference electrode of this design has an essentially constant electrode potential and essentially zero response slope for the duration of its use. As is known in the art of reference electrodes, the total electrode potential is the sum of the potential difference between the electrode and integral salt-bridge electrolyte and the liquid-junction potential difference which is between the salt-bridge electrolyte and the test solution. The constant electrode potential of such prior-art reference electrodes is achieved firstly because the potential determining chloride concentration of the salt-bridge electrolyte at the silver—silver chloride electrode surface remains essentially fixed for the duration of use. This is achieved both because the rate of chloride efflux from the reservoir into the test solution is sufficiently small because of the constrained-flow junction and because the electrolyte reservoir is sufficiently large. Secondly, the response slope of such salt-bridge reference electrodes is also small when the liquid junction potential difference is small as is the case when the salt-bridge electrolyte contains a concentrated salt with anions and cations of nearly equal mobility, such as with the use of a concentrated potassium chloride electrolyte.

Planar potentiometric salt-bridge reference electrodes of the prior art have used the same approach as the classical salt-bridge reference electrode described above. U.S. Pat. No. 4,592,824 describes a planar silver—silver chloride electrode on a planar silicon substrate, and a silicon cover-plate including a micro-fabricated cavity and porous region. The cavity becomes the integral salt-bridge reservoir when it is filled with concentrated potassium chloride before use. The porous silicon element forms the region of the constrained-flow liquid junction that contacts the test solution. Similarly, U.S. Pat. No. 4,682,602 describes a planar silver—silver chloride electrode and a cover layer defining a cavity over the electrode. The cavity, when filled with electrolyte, becomes the integral salt-bridge reservoir. There is a small aperture providing a flow-constraining liquid junction contact to a test solution. U.S. Pat. No. 5,385,659 describes a planar silver—silver chloride with a micro-fabricated, elongated cavity in a cover plate. When the elongated cavity is filled with electrolyte it becomes the integral salt bridge reservoir. The flow of electrolyte out of the salt-bridge is constrained because the cavity is elongated and its opening is small. These and other prior-art planar reference electrodes with integral electrolyte cavities are relatively complex assemblies and therefore costly. They must be filled with concentrated salt-bridge electrolyte before use, or, if filled in the factory, they must be stored wet. Consequently, they are impractical for unit-use applications.

U.S. Pat. No. 4,342,964 describes a fluidic cassette for blood measurement containing a dry-stored silver—silver chloride electrode without an integral salt-bridge electrolyte over-layer and a spaced apart indicator electrode. In use a calibrator solution is introduced over the pair of electrodes serving to calibrate the indicator electrode prior to its subsequent exposure to the test solution. The calibrator solution also fills an empty cavity region of the cassette over the silver—silver chloride electrode and remains there to form a liquid junction with the test solution when it is subsequently introduced into the cassette. Thus, this patent teaches how to automatically fill a reference electrode's salt-bridge reservoir without significantly adding to the complexity of the reference electrode itself, because the device already requires a calibrator solution and the patent teaches that the calibrator solution can be the same as the salt-bridge filling solution. However there is added fluidic complexity and cost, and the significant limitation on this invention is that there is no single composition of the calibrator solution that is satisfactory both to accurately calibrate the indicator electrode and provide for a low-response liquid junction. For acceptable performance in blood it is known in the art that the salt-bridge electrolyte should have a potassium chloride concentration of about 1M or even larger for the liquid junction potential component of the reference electrode to be acceptably small and constant. Known calibrator solutions for blood do not provide this concentration Janata in *Solid State Chemical Sensors*, Janata J. and Huber R. J. (eds.), Academic Press Inc., Orlando 1985, pp101–103, describes an ion-sensitive field effect reference electrode with an integral salt-bridge reservoir formed by a hydrophilic gel layer coating the electrode. Sinsabaugh et al. in *Proceedings, Symposium on Electrochemical Sensors for Biomedical Applications*, Vol 86–14, Conan, K. N. L. (ed.), The Electrochemical Society, Pennington, N.J. 1986, pp66–73, describe a planar reference electrode consisting of a silver—silver chloride electrode over-coated by an integral salt-bridge reservoir formed by a latex membrane. In this device there are in total three coating steps onto the conductor element and its support. The Janata and Sinsabaugh devices were intended for multi-use sensor applications utilizing a calibrator solution. In a typical measurement, the reference electrode, with its salt-bridge reservoir over-layer, and a spaced-apart indicator electrode are first immersed in a calibrator solution. The integral reservoir equilibrates to the concentration of the calibrator solution. When the electrode-pair is then immersed in a test solution, the indicator electrode responds rapidly but, because of its integral constrained-flow reservoir, the potential difference between the silver—silver chloride and the salt-bridge electrolyte over-layer responds slowly. If the reservoir thickness is sufficient (several hundred micrometers) the response is slow enough to constitute a constant potential over the time that the indicator electrode responds (approximately 10s). During multiple uses, the composition of the salt-bridge gradually approaches the concentration of the calibrator and test solutions in which it is immersed. These reference electrodes in multi-use application are once again limited in utility for accurate blood measurements because the liquid junction component of the reference electrode potential is not sufficiently small or constant due to the salt-bridge reservoir concentration being too low. Both these papers are silent on the use of their salt-bridge reservoirs as dry-reagent formulations in unit-use reference electrodes. Both papers are silent on the incorporation of redox chemicals into the salt-bridge reservoirs and the use of such in reference electrodes constructed with salt-bridges coating metals. The Sinsabaugh paper is also silent on the water vapor transport properties of their heterogeneous membrane formulation.

Because of the complexity of manufacture of reference electrodes containing integral fluid reservoirs and because of the difficulty of their storage and preparation for use, a dry-reagent reference electrode is highly desirable for unit-use applications. An integral dry-reagent salt-bridge reservoir that contains only dry salts must first acquire water so that the salt-bridge reservoir can 'wet up' to its operational concentration. In all of the above-mentioned prior-art devices the transport of species through the salt-bridge reservoir and from the salt bridge to the contacting solution is through an electrolyte phase. Water influx for wet-up if the prior-art devices were initially prepared in the dry state is through the same path as potassium chloride efflux. Thus, in a device featuring a constrained flow salt-bridge design with a sizeable reservoir that is required to maintain constancy of chloride concentration at the silver—silver chloride surface, the time for water uptake also will be large. Also, the potassium chloride of the salt bridge electrolyte will escape from the reservoir into the solution while the reservoir is acquiring water from the solution for its wet-up. Therefore, reference electrodes with dry reagent reservoirs according to the above prior have not been successfully deployed in unit-use applications.

The above wet-up problem was addressed in U.S. Pat. No. 4,933,048, which describes a dry-reagent salt-bridge reference electrode made by planar micro-fabrication. In this device there is a first insulating layer on a planar substrate that supports a conductor for connection to a measuring circuit. A second insulating layer covers the conductor except in a region that defines the electrode opening. There are films of silver, then silver chloride formed over the conductor in the electrode region. A solid hydrophilic material containing potassium chloride is formed over the silver chloride. This layer constitutes the integral salt-bridge reservoir. In this device, the salt-bridge reservoir extends well beyond the silver—silver chloride electrode edge and is further coated by a hydrophobic water vapor-permeable over-layer, except for a region of the salt bridge that is far removed from the silver—silver chloride where the salt-bridge contacts the test fluid defining the liquid junction. This unit-use salt-bridge reference electrode was designed to rapidly wet-up during use from its dry storage state, and to essentially retain a constantly high concentration of potassium chloride in the integral salt-bridge reservoir for a period after full wet-up and through the time of the measurement. These desired properties are obtained in the device of the '048 patent by providing a short diffusion path for rapid water influx into the integral reservoir through the water vapor-permeable over-layer and a long diffusion path for the potassium chloride in the salt-bridge along the length of the integral reservoir. In use, water necessary for the proper function of the salt bridge is rapidly incorporated into the initially dry potassium chloride layer within a few seconds by diffusion through the gas permeable over-layer. The concentration of the internal salt-bridge electrolyte rapidly reaches a steady state value after a wet-up period of a few seconds, which is maintained for a period sufficient to perform the potentiometric measurement. However, this device is complex to manufacture, consisting of five layers on top of the conductor element and its insulating support.

U.S. Pat. No. 4,431,508 describes a graphite reference electrode with a hydrophilic coating containing a redox couple manufactured with non-planar conventional technology.

In summary, planar reference electrodes of the prior art consist of a silver—silver chloride electrode contacting an integral salt-bridge electrolyte reservoir consisting of concentrated potassium chloride. These devices are either manufactured with water already incorporated into the salt-bridge reservoir, or, are dry-reagent devices with a gas permeable coating that facilitates water transport into the salt bridge. The salt bridge makes connection to the test solution through a small, flow-constraining orifice or other flow limiting physical constriction fabricated on the device in planar technology. The connection of the salt bridge to the test solution is at a point removed from the silver—silver chloride electrode, so that an integral reservoir of electrolyte is present between the solution and the electrode Prior-art planar electrochemical sensors including planar salt-bridge reference electrodes require numerous electrode materials and membrane coatings to achieve the desired functionality. Prior-art planar electrochemical sensors, therefore, are still complicated and relatively expensive to produce. In addition to being relatively costly, such devices generally still also require at least a single, in-use calibration fluid step to achieve a performance equivalent to laboratory analyzers. Even sensor designs that use micro-fabrication technology (U.S. Pat. Nos. 5,063,081 and 5,514,253 for example) with its high levels of dimensional precision have failed to achieve the standard of performance (reproducible slope and intercept of the response) required for use without a calibration step in a fluidics-free analyzer.

Thus there remains a significant need to provide planar electrochemical sensor devices for precise quantitative analysis which are sufficiently simple in design and construction for use as cost-effective unit-use devices.

SUMMARY OF THE INVENTION

It is an object of this invention to provide unit-use planar electrochemical sensors of simplified construction and their electrode components.

It is a specific object of the invention to provide unit-use salt-bridge reference electrodes manufactured in planar technology.

It is an object of this invention to provide unit-use salt-bridge reference and indicator electrodes for use with a single calibrator solution.

It is an object of this invention to provide unit-use salt-bridge reference and indicator electrodes for use with a single calibrator solution, wherein the electrodes and calibrator are all contained within a single, unit-use housing. This invention teaches such integral diagnostic devices. When used with a card read-out device the integral diagnostic device including an on-board calibrator and electrodes of this invention provide an analyzer capable of delivering very inexpensive quantitative test results.

These objects are achieved in accordance with the invention by providing planar salt-bridge reference electrodes constructed with at least a single heterogeneous membrane for supporting rapid gas and water vapor transport through a hydrophobic gas permeable path and electrolyte transport through a hydrophilic path.

Heterogeneous membranes in accordance with the present invention are made of a formulation that comprises an intimate admixture of at least two component phases, a hydrophilic electrolyte-containing compartment that supports non-volatile species transport and chemical reaction and a hydrophobic compartment that supports gas and water vapor transport. Such a heterogeneous membrane in accordance with the invention can be used as an element of a unit-use sensor of very simple construction.

Highly gas permeable polymers such as siloxanes, in particular poly-dimethyl siloxane or derivatives thereof, are preferably used in the heterogeneous membranes of the invention in intimate admixture with hydrophilic components. The intimate admixture of the resultant heterogeneous membrane comprises a gas and water vapor transport path through the hydrophobic siloxane compartment and a tortuous transport path for electrolyte salts through the hydrophilic compartment.

The invention teaches methods of preparation of heterogeneous membranes from aqueous emulsions of siloxanes.

In a preferred embodiment, an electrode of this invention includes a single conductor element for connection to a measuring circuit which conductor is coated by a first, hydrophilic reservoir layer, which in turn is coated by a second, heterogeneous membrane layer. The heterogeneous membrane provides the dual electrolyte and gas-conducting properties required for proper device function. In this embodiment of the invention, the first, hydrophilic layer is in contact with the electrode and constitutes an internal electrolyte that contains the reagents required for the electrode reaction (a potential determining redox reagent, such as potassium ferrocyanide, and a salt of equi-mobile ions such as potassium chloride), and the heterogeneous membrane provides gas transport to the internal electroltye through its hydrophobic compartment as well as electrical contact between the internal electrolyte and the test solution by electrolyte transport through the hydrophilic compartment. The hydrophilic compartment of the heterogeneous membrane forms the reference electrode's liquid junction and it contains at least a salt of equi-mobile ions such as potassium chloride.

In another preferred embodiment, the electrode of this invention includes a single conductor element for connection to a measuring circuit which conductor is coated with a heterogeneous membrane. The heterogeneous membrane preferably provides within a single element the electrolyte reservoir and the dual electrolyte and gas-conducting properties required for proper device function. This is in contrast to the multiple elements contained in prior-art devices. In this preferred embodiment, the heterogeneous membrane's hydrophilic compartment serves as the internal electrolyte reservoir and liquid junction. It contains at least a redox reagent and a salt of equi-mobile ions. The heterogeneous membrane's hydrophobic compartment provides for rapid gas transport to the electrode surface. Thus this embodiment achieves in a single membrane device a disposable salt-bridge reference electrode that can be manufactured at very low cost.

It is a further object of the invention to provide single membrane as well as dual membrane compositions for use in salt-bridge reference electrodes. These compositions are achieved through the engineering of multiple transport paths into heterogeneous membrane materials.

It is yet another object of the invention to provide design principles for the achievement of the desired transport properties of the heterogeneous membrane.

It has been surprisingly discovered that the simplified sensor membrane manufacturing processes according to this invention can be advantageously combined with low cost smart card-based electrode modules disclosed in a co-pending patent application U.S. Ser. No. 09/871,823. These substrates are low cost stamped laminations of gold-coated copper with epoxy foils. The electrode material is gold in these modules. Thus, it is an object of this invention to provide disposable sensors with membrane compositions and methods of construction suitable for fabrication on laminated foil electrodes.

It is still another object of the invention to provide electrode sensor arrays fabricated on an array of contacts with a contacting material common to all of the electrodes in the array and with only a single membrane per electrode in the array.

It is an essential feature of conventional sensors that the integral internal electrolyte element is large enough and sufficiently well isolated from the test solution that it behaves as a reservoir which immobilizes the sensor's reagents within it. In conventional sensors, the reservoir's reagent composition thus remains essentially fixed for the duration of a measurement (except in the first few seconds during wet-up of dry stored devices and except of course for the chemical reaction involving the species to be analyzed whose compositional changes constitute the sensor reaction), and contaminants from the test solution are excluded from and thus at low concentration in this internal electrolyte reservoir. Indeed, it is most often the case that the composition of reagents in the electrolyte reservoir element at the electrode surface remains fixed for numerous measurements because these devices have been typically designed to be reusable. In some prior-art devices, the sensor's internal electrolyte element is completely isolated from the test solution by one or more layers that selectively transport only the species to be analyzed. For example, prior-art dissolved carbon dioxide and oxygen sensors consist of internal electrolyte elements covering the sensors' electrodes and a selectively gas-permeable but electrolyte impermeable over-layer on top of that. In other prior-art devices where there is direct contact between the internal electrolyte element and the test solution, the internal electrolyte adjacent the electrode is far removed from the point of contact with the test solution.

In contrast, in the devices of the current invention, there is no provision for the complete isolation of the electrode's internal electrolyte from the test solution. In the preferred embodiment, the reagent composition of the electrolyte component of the heterogeneous membrane in close proximity to the electrode surface actually changes with time during use of the device. For example, reagents diffuse out of the heterogeneous membrane into the test solution or contaminants permeate into the membrane from the test solution. Furthermore, the initial amount of internal electrolyte within the heterogeneous membrane is often not sufficiently large to constitute a reservoir maintaining a constant composition of the immobilized reagents during use. Surprisingly, even though numerous elements that were necessary in prior-art devices have been omitted from the simplified devices of this invention, the important characteristics defining quantitative sensing performance are retained. The preferred devices can exhibit fast wet-up (important if the device is stored dry prior to use), at least reproducible response intercepts if they are polarographic devices and at least reproducible response slopes if they are potentiometric devices, and sufficient freedom from interferences. Thus these very simple devices of the invention can be incorporated into an analyzer requiring only a single in-use calibration fluid.

As discussed above, sensors with porous heterogeneous membranes according to this invention will inevitably exhibit loss of reagents from the device into the test solution.

Furthermore, some contaminants or electrochemical interferents can permeate from the test solution into the device. It is surprising that measurements can be made with devices of the invention in which chemical compositions of the reagents are changing at the electrode surface, even after full wet-up of the device. Thus, it is the object of this invention to teach heterogeneous membrane compositions and properties that are tolerant to these deleterious effects, and to teach methods of measurement using electrodes incorporating heterogeneous membranes that lose specific contents into the test solution or acquire contaminants from the test solution during use. This invention further teaches the range of acceptable transport properties of a heterogeneous membrane for electrochemical sensing. In the preferred embodiment, it is required that the diffusion coefficient of water vapor should be at least 10 times faster than the diffusion coefficient of aqueous electrolytes and other water soluble species, and preferably greater than 50 times faster. More specifically, gas and water vapor diffusion preferably occurs at faster than $5\times10^{-6}$ $cm^2$ $sec^{-1}$ and electrolyte salt diffusion at less than $5\times10^{-7}$ $cm^2$ $sec^{-1}$.

It is also surprising that the reproducible performance attributes of devices of the invention are robust to variations of the devices' physical dimensions. The approach in accordance with this invention therefore allows a loosening of the specification on dimensional control and compositional precision and allows simpler manufacturing processes and fewer materials and process steps.

BRIEF DESCRIPTION OF THE DRAWINGS

Preferred embodiments of the invention will now be further described by way of example only and with reference to the attached drawings, wherein

FIG. 5A is a graph of the simulated salt concentration at the inner membrane surface versus time for a reference electrode according to this invention;

FIG. 5B is a graph of the simulated electrode voltage versus time of a of reference electrodes according to the invention;

FIG. 6A is a graph of the experimental membrane resistance versus time for reference electrodes according to the invention;

FIG. 6B is a graph of the simulated membrane resistance versus time of reference electrodes according to the invention;

FIG. 7 is a graph of the experimental reference electrode response (open squares) versus time and the computed reference electrode response (solid and dashed lines) from the simulation;

DETAILED DESCRIPTION OF THE PREFERRED EMBODIMENTS

Figure 1A:
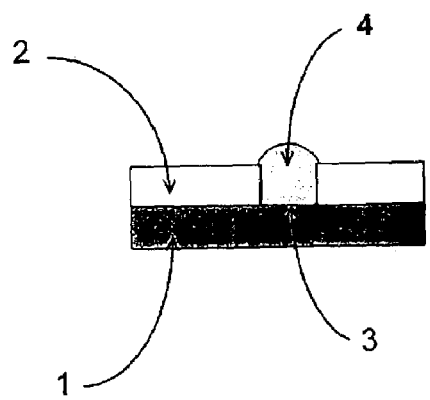
FIG. 1A is a principle schematic cross-section through an electrode in accordance with the invention.

In the most general construction as shown in FIG. 1A, electrodes in accordance with the invention include a planar electric conductor 1. The planar conductor is coplanar with, and contacted by an insulator 2 with a thoroughgoing aperture 3 defining an electrode region. A heterogeneous membrane 4 is constructed for direct contact with an aqueous sample fluid, is located in the electrode region and extends through the aperture 3 for electric contact with the conductor 1. The heterogeneous membrane comprises a hydrophobic gas permeable compartment and a hydrophilic electrolyte permeable compartment.

Heterogeneous Membrane Electrodes

The heterogeneous membranes according to this invention are materials consisting of an intimate admixture of two components. The first is a hydrophobic gas permeable material component, the second is a hydrophilic electrolyte conducting component. In a preferred composition, the hydrophobic component is in excess by volume over the hydrophilic component. The essential transport property of the heterogeneous membrane of the invention is that the membrane diffusion coefficient for gas through the hydrophobic compartment (water vapor for wet-up) is significantly larger than the membrane diffusion coefficient of species dissolved in the water (ions and neutral non-volatile molecules) contained within the hydrophilic compartment. We have found that sensors can be made with adequate performance attributes when the ratio of these diffusion coefficients is about 10, but preferably the ratio should be at least 50 and better still greater than 100.

Preferably the hydrophobic component of the admixture is a polymer of high vapor permeation rate. Such polymers are well known in the art. Examples include poly-siloxanes, poly-organo-phosphazenes, and poly-1 trimethyl-silyl-1-propyne and poly-4-methyl-2-pentyne. The hydrophilic component of the admixture is a hydrophilic compartment comprising some or all of the following: emulsifiers, hydrophilic polymer binder, electrolyte salts and other optional dissolved components depending on the sensor. Hydrophilic polymers are well known in the art. Examples include polyvinyl alcohols, poly-hydroxymethacrylates, poly-acrylamides, poly-saccharides, cellulosic polymers and gelatins. Other optional constituents of the hydrophilic compartment include cross-linkers, catalysts, redox agents, buffers and surfactants that will be incorporated into the membrane upon preparation.

Heterogeneous membranes are prepared by casting from solutions and suspensions of the membrane materials in volatilizable solvents. Membranes can be cast 1: from an aqueous casting-solution containing dissolved hydrophilic components and the hydrophobic component either as a suspension of solid particles of the hydrophobic polymer resin or as an emulsion of suspended liquid hydrophobic polymer or monomer. The liquid suspension can be polymer resin dissolved in a hydrophobic solvent or it can be solvent-free liquid polymer or monomer. Monomers or low molecular weight liquid precursors in the suspension can be cross-linked into a solid hydrophobic polymer membrane upon casting if the hydrophobic polymer contains reactive groups that can cross-link or by addition of appropriate cross-linking additives to the emulsion. 2: from a non-aqueous casting solution containing dissolved hydrophobic polymer and the hydrophilic component dissolved in water in an emulsion with the non-aqueous solvent.

In principle, any method of deposition of a coating from a volatilizable liquid is feasible. The membrane might be cast onto a planar electrode using any of the methods known in the art such as dispensing through a nozzle, transferring a drop onto the electrode from a solid tip, spin coating, dip coating, spray coating, screen printing and the like. We have used primarily pin-transfer and nozzle dispensing techniques.

The specific device dimensions and composition of the heterogeneous membrane element will be dependent on the type and function of the electrode of this invention.

Devices of this invention encompass sensors that function as potentiometric salt bridge reference electrodes, but the design principles can also be extended to other sensor types such as potentiometric and polarographic gas sensors and enzyme electrodes.

Figure 1B:
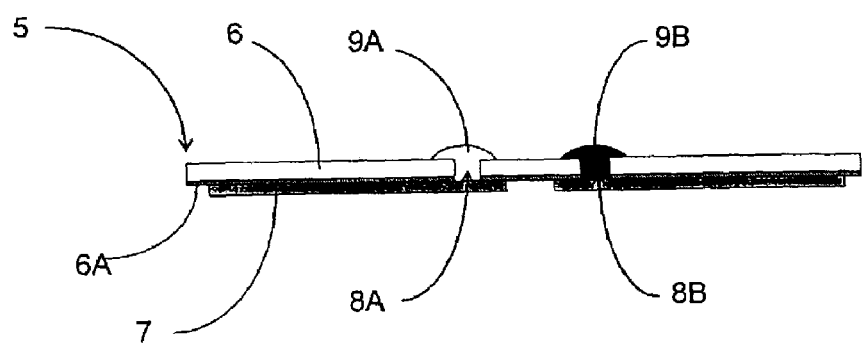
FIGS. 1B and 1C are horizontal cross-sections of preferred embodiments of the device according to this invention.
Figure 1C:
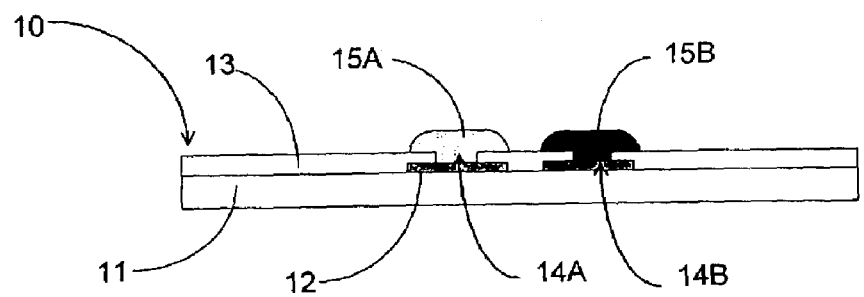

All of the various principal electrode types achievable with the heterogeneous membrane technology of the current invention are depicted in the preferred embodiment of the invention shown in FIG. 1B and an alternative embodiment shown in FIG. 1C.

In these figures the specific compositions and dimensions of the elements will depend on the specific electrode type. As will be apparent from the following detailed descriptions of each of the different electrode types, the composition, structure and dimensions of the heterogeneous membranes determine the functional properties of the respective electrode.

FIG. 1B depicts a first preferred embodiment which is a laminated foil electrode, while FIG. 1C depicts another preferred embodiment, a coated insulating substrate electrode. Both figures illustrate a pair of electrodes on a single substrate to show how multiple electrodes can be produced on a single substrate. It is clearly contemplated in this invention that there could be numerous different combinations of electrodes on a single substrate as determined by the test application. For example, a test device for blood gases (pH, dissolved carbon dioxide and dissolved oxygen) would consist of an array of 4 electrodes on a substrate (indicator electrodes for pH and the two dissolved gases and a common salt-bridge reference electrode). A glucose test device would be an array of two electrodes on a substrate and so on.

The laminated foil embodiment of FIG. 1B shown in cross-section includes an electrode module with a pair of electrodes. As described in detail in co-pending U.S. patent application Ser. No. 09/871,823. The electrode module 5 includes an insulator foil 6 laminated with a conductor foil 7 and optional adhesive 6A therebetween. Apertures 8A and 8B extended through the insulator and define the position of the two electrodes. Coatings 9A and 9B are applied over the apertures and extend thereinto with overlap onto the insulator. The coatings are in electrical contact with the conductor foil 7.

The coated insulating substrate embodiment of an electrode module 10 is shown in cross-section in FIG. 1C including a pair of electrodes. A planar insulating substrate 11 supports two conductor films 12 coated by an insulating over-layer 13. Apertures 14A and 14B extend through the insulating over-layer and define the respective position of the two electrodes. Coatings 15A and 15B extend into the apertures, overlap onto the insulating over-layer and make contact to the conductors 12.

Coatings 9A and 9B of FIGS. 1B and 15A and 15B of FIG. 1C are heterogeneous membrane elements according to this invention Heterogeneous Membrane Transport Properties Consideration of the membrane's transport properties is needed to better understand the design rules for the selection of materials and composition of a heterogeneous membrane according to this invention. To model the transport properties of the heterogeneous membrane, one needs to know the transport properties of its individual components and the nature of their admixture, particularly the relative volume of the hydrophobic and hydrophilic components, the characteristic dimensions of the hydrophilic compartment's transport paths and the tortuosity of the transport paths created when the two components are intimately admixed.

The tortuosity of a membrane's transport path describes the reduced rate of species diffusion relative to diffusion through a slab of pure material. In a heterogeneous membrane of this invention the tortuosity can be modeled by the increased path length for transport of a continuous path or by the reduced rate of particle transport from isolated islands within a discontinuous path. Both such models of transport are well known in the art of membrane transport.

A heterogeneous membrane of this invention is a slab of geometric area A and geometric thickness L and volume $V=AL$ which comprises a volume $V_G$ of gas permeable polymer of the hydrophobic compartment and $V-V_G=V_H$ of a hydrophilic compartment.

The heterogeneous material has two transport paths through the thickness of the membrane. There is a first transport path for gas and water vapor through the hydrophobic polymer compartment. The hydrophobic polymer is a material characterized by a gas solubility $S_G$ moles cm$^{-3}$ atm.$^{-1}$ and a gas diffusion coefficient $D_G$ cm$^2$ sec$^{-1}$. When equilibrated with water at a temperature T there are $S_G P$ moles of water per cm$^3$ of the hydrophobic compartment where P in atmospheres is the saturated vapor pressure of water at T. The hydrophobic gas transport path is characterized by an effective area $A_G$, and an effective length $L_G$. The ratio $L_G/L > 1$ characterizes a longer transport path for gaseous permeant than the geometric thickness. The ratio $(L_G/L)^2 = \tau_G$ characterizes the tortuosity of the gas permeant path. For a heterogeneous membrane in which the predominant volume component is the hydrophobic compartment, $V_G/V > 0.5$, the tortuosity will be in the range $1 < \tau_G < 2$. The effective diffusion coefficient of gas through the gas permeable path of the heterogeneous membrane is $D_{G,M}$ given by $D_{G,M} = D_G/\tau_G$ where the effective diffusion coefficient relative to the membrane is less than the diffusion coefficient in a slab of the pure hydrophobic polymer $D_G$ by the tortuosity factor $\tau_G$. The preferred gas permeable material selected was poly-dimethyl siloxane (PDMS) and derivatives thereof.

Published data for gas solubility and diffusion coefficient for PDMS at room temperature is shown in the table below.

A second transport path for electrolyte salts and non-volatile molecules is through the hydrophilic compartment. The hydrophilic compartment is characterized by a solubility of water $S_H$ moles cm$^{-3}$ atm.$^{-1}$. When equilibrated with water at a temperature T there are $S_H P$ moles of water per cm$^3$ of volume of the hydrophilic compartment where P in atmospheres is the saturated vapor pressure of water at temperature T. The transport path is characterized by an effective area $A_H$, and an effective length $L_H$. The ratio $L_H/L > 1$ characterizes a longer transport path than the geometric thickness. The ratio $(L_H/L)^2 = \tau_H$ characterizes the tortuosity of the hydrophilic path. For a heterogeneous membrane in which the minority volume component is the hydrophilic compartment ($V_H/V < 0.5$) the tortuosity can be large and dependent on the nature of the admixture of hydrophobic and hydrophilic components. When the amount of hydrophilic component in the heterogeneous membrane is large, the hydrophilic compartment comprises continuous connected conduction paths within the heterogeneous membrane and $\tau_H$ will be on the order of unity. When the amount of hydrophilic component in the membrane is small, the hydrophilic compartment's paths are tortuous or even discontinuous and $\tau_H$ will be large, and when they are isolated, $\tau_H$ approaches infinity and there is no hydrophilic conduction path through the membrane.

The hydrophilic compartment is further characterized by a model of water-containing micro-capillary pores contained within a continuum hydrophilic matrix. The volume of aqueous electrolyte in the hydrophilic compartment is $V_E$ and the volume of the dry other hydrophilic compartment's constituents $V_H - V_E$. At equilibrium $V_E / V_H = S_H P / 0.055$, assuming 0.055 moles of water occupy 1 cm$^3$. The electrolyte conduction path within the hydrophilic compartment is characterized by an effective area $A_E$ and an effective length $L_E$. The ratio $L_E/L_H > 1$ characterizes a longer transport path for electrolyte diffusant through the pores of the hydrophilic compartment than the hydrophilic path length. The ratio $(L_E/L_H)^2 = \tau_P$ characterizes the tortuosity of the electrolyte pores relative to the hydrophilic path. Combining the tortuosity of the electrolyte path in the hydrophilic matrix and the tortuosity of the hydrophilic matrix path within the heterogeneous membrane gives the total tortuosity of the electrolyte path with respect to the membrane as $(L_E/L)^2 = \tau_P \tau_H = \tau_E$. It is well known in the art of hydrophilic polymer gels that $\tau_P$ the tortuosity of the electrolyte path through the pores of a hydrophilic polymer can be very large depending on the equilibrium water content of the hydrophilic polymer and the degree of cross-linking of the matrix, so that typically $1 < \tau_P < 10000$ when $0.01 < V_E/V_H < 1$. Consequently it is possible to formulate hydrophilic matrixes where the equilibrium water content is of the order of a few percent of the volume of the hydrophilic matrix and the diffusion coefficient of aqueous diffusants in the hydrophilic matrix is up to 1000 times lower than the diffusion coefficient in water. (see for example Hydrogels in Medicine and Pharmacy, CRC Press, N. A. Peppas ed., Vol 1 1986). The effective diffusion coefficient of a species dissolved in the pore water of the hydrophilic compartment of a heterogeneous membrane is $D_{EM}$ given by $D_{EM} = D_E / \tau_E$ where the effective diffusion coefficient relative to the heterogeneous membrane is less than the diffusion coefficient in a slab of pure aqueous electrolyte $D_E$ by the tortuosity factor $\tau_E$. For diffusion of small molecules through a hydrophilic polymer containing $V_E/V_H$ volume fraction of water, the diffusion constant of a salt through the hydrophilic compartment $D_H$ is less than the diffusion coefficient in water $D_W$ by a factor given by $$\frac{D_H}{D_W} = \frac{1}{\tau_P} = e^{N\left(1 - \frac{V_H}{V_R}\right)} \qquad \text{Equation 1}$$

where N is a constant close to unity (see for example H. Yasuda et al. "Permeability of Solutes through Hydrated Polymer Membranes" in Die Makromolekulare Chemie 118 (Nr. 2858), (1968) p19–35). The relative diffusion coefficient factor is related to the previously defined tortuosity. The literature of hydrophilic polymers (of which the two above examples are typical) provides numerous examples of chemical cross-linking methods to achieve hydrophilic polymer matrixes with different equilibrium water uptake and different salt diffusion coefficients.

The transport of gas and water vapor through the heterogeneous membrane is primarily by diffusion through the gas permeable compartment and then by partitioning between the gas permeable compartment and the hydrophilic compartment within the membrane. The partitioning of water between the hydrophobic and hydrophilic compartments' pores can be assumed to be an equilibrium process when the transport of water across the hydrophobic/hydrophilic pore boundary is rapid compared to transport along the pore through the thickness of the membrane. The characteristic distance of hydrophobic to hydrophilic pore transport is on the order of the pore size of the admixture (on the order of 1 micrometer) which is small compared to the membrane thickness (on the order of 100 micrometers). When transport of water from the hydrophobic compartment to the hydrophilic compartment is slower, such as when the characteristic pore size of the heterogeneous admixture is large, an additional time constant is introduced to the water absorption kinetics.

The transport of electrolyte is through the water-filled capillary pores within the hydrophilic compartment only.

To better understand the required range of transport properties of the heterogeneous membranes of this invention, we have performed simulations of the invented electrodes' response characteristics using a finite difference numerical method. With this method we solved the equations describing the simultaneous transport of the various species through the heterogeneous membrane. The results of this simulation are the species' concentrations (water, ions other solutes and gases) within the membrane versus position and time. These concentration values are then used to calculate the electrical responses of electrodes using heterogeneous membranes of this invention. These numerical simulations and the data from exemplar heterogeneous membrane electrodes made in accordance with this invention are presented below to teach how to best practice the invention.

Diffusion of Water into Heterogeneous Membranes

It is generally the case that prior to incorporation of water into a dry reagent electrochemical sensor 1: The device exhibits significant noise. Absent water, the bulk membrane components of the device are not yet sufficiently ion conducting, and their electrical resistance is large; 2: The electrode potentials and response slopes of potentiometric electrodes including potentiometric reference electrodes are erratic and vary rapidly over time. Prior to wet-up, electrochemical reactions at electrode interfaces are slow and the electrode potential is said not to be well poised; 3: Polarographic devices exhibit low electrode current and large capacitive transient currents prior to wet-up. Consequently there is an initial time in which a dry reagent electrochemical sensor should be immersed in an aqueous solution during which time the device absorbs water prior to achieving its functioning state as a sensor. This is called the wet-up time.

Wet-up of heterogeneous membranes of this invention is by rapid water diffusion through the gas permeable hydrophobic compartment and then by rapid partitioning between the gas permeable compartment and the hydrophilic compartment within the heterogeneous membrane.

We have computed the wet up of heterogeneous membranes as follows: First we calculate the time and position dependence of water diffusing into the membrane through the hydrophobic compartment. The numerical solution of the transport equations used an initial condition of $1 \times 10^{-5}$ moles $cm^{-3}$ corresponding to the initial equilibrium water content of a hydrophobic polymer with water solubility $1 \times 10^{-3}$ moles $cm^{-3}$ $atm.^{-1}$ initially stored in an ambient of 0.01 atmospheres of water vapor (corresponding to normal room air at 23° C. and 40% RH). The solubility and diffusion coefficient used in this calculation are those shown in Table 1 for PDMS which is exemplar of a highly gas permeable polymer. The amount of water in the hydrophilic compartment is obtained by computing the equilibrium partitioning between the hydrophobic and hydrophilic compartments (assuming a value for the equilibrium water uptake of the hydrophilic compartment). The amount of water versus time at the inner membrane surface at the electrode is thus obtained. The time to 95% water uptake at the inner surface is then obtained from the computed time transient.

Figure 2A:
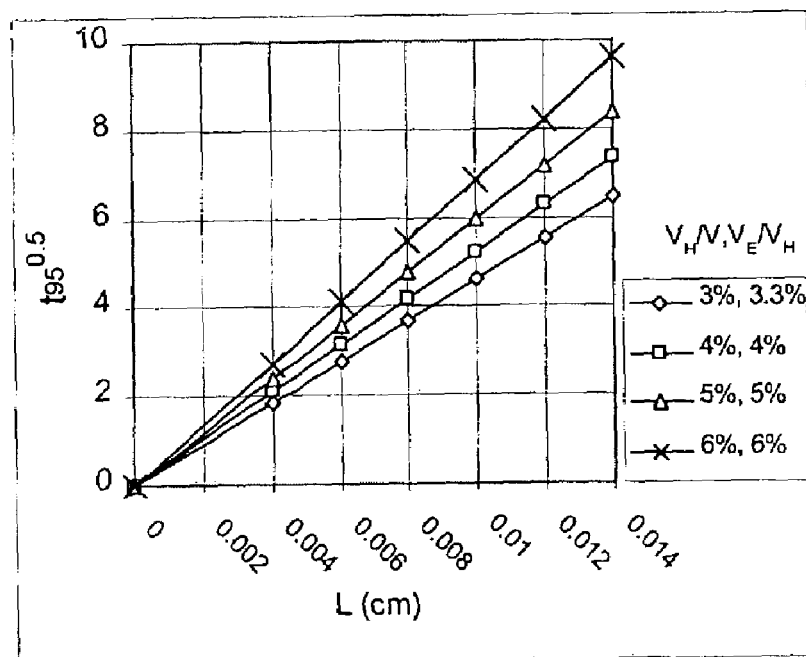
FIG. 2A is the simulated time to 95% wet-up of a heterogeneous membrane versus membrane thickness.
Figure 2B:
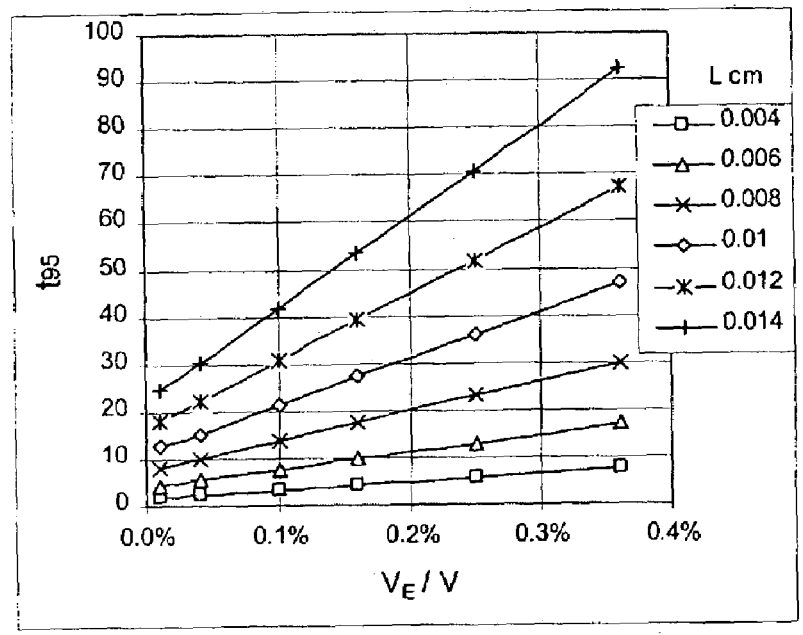
FIG. 2B is the simulated time to 95% wet-up of a heterogeneous membrane versus equilibrium water content.

The calculated time to 95% wet-up for a number of heterogeneous membrane compositions and thicknesses is shown in FIG. 2. The volume percent of water in the membrane given by $V_E/V \times 100\% = V_E/V_H \times V_H/V \times 100\%$ is the product of the volume fraction of water in the hydrophilic component multiplied by the volume fraction of the hydrophilic compartment in the heterogeneous membrane. The wet-up time increases linearly with the amount of water in the wetted-up membrane (FIG. 2A). The wet-up time increases as the square of the membrane thickness (FIG. 2B)

Typical membrane compositions according to this invention have $0.01 < V_H/V < 0.1$ and $0.01 < V_E/V_H < 0.1$ so that $0.0001 < V_E/V < 0.01$. A typical membrane thickness is 0.01 cm, so that $t_{95}$ of a typical heterogeneous membrane is in the range $12 < t_{95} < 60$ seconds when it contains a typical hydrophobic gas permeable polymer whose water solubility is $1 \times 10^{-3}$ moles $cm^{-3}$ $atm.^{-1}$ and diffusion coefficient is $1 \times 10^{-5}$ $cm^{-5}$ $sec^{-1}$.

Potentiometric Salt-Bridge Reference Electrode with Heterogeneous Membrane

Figure 3A:
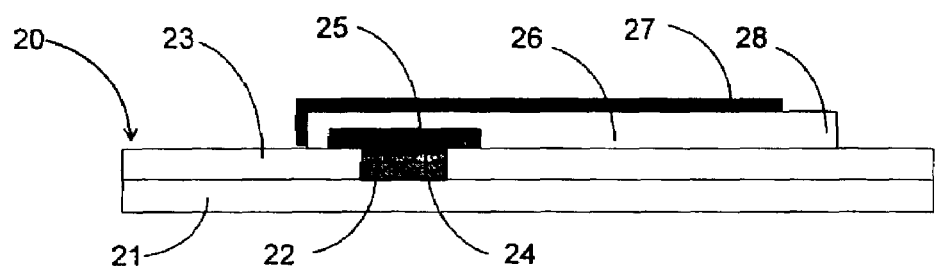
FIGS. 3A and 3B are horizontal cross-sections of a prior-art planar salt-bridge reference electrodes.
Figure 3B:
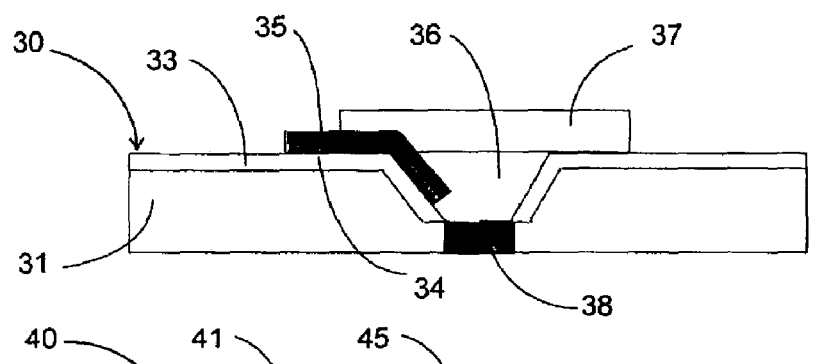
Figure 3C:
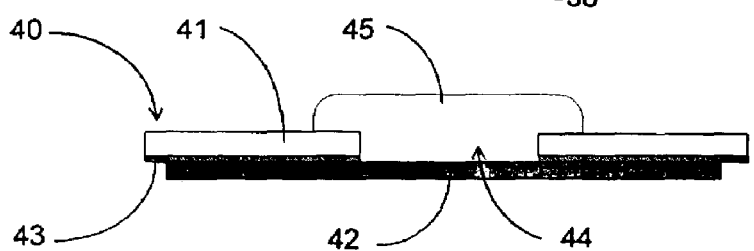
FIG. 3C is a horizontal cross-section of a salt-bridge reference electrode according to one embodiment of this invention.

FIGS. 3A and 3B show horizontal cross-sections of prior-art planar salt-bridge reference electrodes while FIG. 3C illustrates a preferred horizontal section of a preferred saltbridge electrode of the invention. The device 20 depicted in FIG. 3A is an extended salt bridge planar reference electrode of prior-art patent U.S. Pat. No. 4,933,048. It comprises a planar substrate 21, with a micro-fabricated conductor 22 contacting a micro-fabricated silver 24 and silver chloride 25 electrode through a hole in an insulator layer 23. A thin film hydrophilic matrix 26 containing potassium chloride is micro-fabricated to extend from the electrode to a remote region 28 where there is a liquid junction with the test solution. The hydrophilic matrix film is coated with a micro-fabricated water vapor permeable insulating element 27. The device 30 depicted in FIG. 3B is another planar reference electrode of prior-art patent U.S. Pat. No. 4,592,824. It comprises a planar silicon substrate 31, with a micro-fabricated silver 34 and silver chloride 35 electrode on an insulator layer 33. There is a cavity etched into the silicon which is filled with potassium chloride solution 36 and sealed with a glass cover 37. The integral electrolyte in the cavity makes a liquid junction contact with the test solution through a porous region fabricated in the silicon substrate 38.

In their use, prior-art planar salt-bridge reference electrodes are immersed in the test solution. The integral reservoir of potassium chloride remains at a constant concentration over the silver—silver chloride electrode, thus defining a constant electrode voltage. A salt-bridge electrically connects the silver—silver chloride electrode region to the external test solution.

FIG. 3C shows a horizontal cross-section of a preferred embodiment of the present invention directed to potentiometric salt-bridge reference electrodes.

The embodiment of FIG. 3C is remarkably simple when compared to the complex multi-layer devices of the prior art discussed above. In this embodiment, the planar electrode is a metal only (no metal salt as in the standard silver—silver chloride technology). The metal is the same as the metal contact material. The salt bridge electrolyte is incorporated into a single layer membrane coating consisting of a heterogeneous composition. The electrode module 40 shown in cross-section includes an insulating foil 41 laminated with a conducting metal foil element 42 and optional intermediate adhesive 43. A punched passage 44 through the insulator foil 41 determines the location of the electrode. The heterogeneous membrane 45 consists of a hydrophobic polymeric component that is water vapor permeable (but not permeable to electrolyte) and a hydrophilic, electrolyte permeable component. The hydrophilic component consists of at least a concentrated salt of approximately equi-mobile cations and anions (such as potassium chloride) and a redox active species that participates in an oxidation-reduction reaction at the metal electrode. In a preferred embodiment of this device the electrode is gold, the heterogeneous membrane consists of a siloxane hydrophobic polymer admixed with a hydrophilic component that contains at least potassium chloride and potassium ferrocyanide. Additional components of the hydrophilic compartment of the membrane are hydrophilic polymer binders such as polyvinyl alcohol, and surfactants and pH buffers.

The hydrophobic water vapor permeable compartment of the heterogeneous membrane should be present in sufficient quantity to achieve sufficient and rapid (typically less than 30 seconds) water uptake into the initially substantially dry membrane. The definition of 'dry' used in this disclosure is the absence of water to the extent that the 'dry' hydrophilic compartment has the properties of a quasi-solid rater than a liquid electrolyte, and further that the components of the membrane are chemically stable during shelf storage and do not transport appreciably out of the membrane during storage. The initial condition of the dry membrane might be such as results from storage in a normal 40% relative humidity environment and need not be dry as resulting from a relatively anhydrous (low relative humidity) storage condition. We have stored all exemplar devices described herein at nominal room temperature and humidity (40%+/−10% RH). In use there is an initial (typically less than 30 seconds) rapid water uptake through the hydrophobic compartment upon immersion of the device into the test solution.

In the dry state, the water content of the hydrophilic compartment is relatively small and, in accordance with equation 1, the tortuosity of its conduction paths is large. In consequence the electrical resistance also is large and the devices exhibit noise. The device does not operate as a stable reference electrode until it has wetted-up.

Because this device is intended for use with a potentiometric indicator electrode in a measurement procedure that uses a single calibration fluid, the design specification of an optimally performing salt-bridge reference electrode of the current invention does not require the reference electrode potential (which is the sum of the potential at the electrode due to the potential determining reaction plus the liquid junction potential) to be constant through the course of a measurement, nor constant from device to device. The optimally performing device needs only to exhibit a low response slope to changes in the chemical composition of the test solution. Therefore, it is not necessary that the concentrations of the electrode-potential-determining species (the redox reagent in this example) at the inner boundary of the heterogeneous membrane remain constant during use, only that the concentrations remain in sufficient excess over redox contaminants permeating in from the test solution to constitute the potential determining electrode reaction. Nor is it necessary that the concentrations of the various salt bridge electrolytes remain constant, only that they remain above a threshold concentration consistent with a low liquid junction potential.

During and after wet-up there is continuous depletion of the heterogeneous membrane of those reagents initially incorporated into its hydrophilic compartment (at least potassium chloride and a redox electrolyte) by out-diffusion into the test solution. Thus, the concentration of these reagents in the heterogeneous membrane decreases through the course of the measurement. The initial quantities of reagents in the membrane, the membrane thickness and the permeability of the membrane's hydrophilic compartment will determine the time to deplete the reagents to a critical threshold concentration level. As will be shown below, so long as the salt diffusion coefficient is sufficiently low, the membrane's concentration of potassium chloride stays above a threshold concentration up to the time of the measurement (a typical measurement time being of the order of 10 to 200 seconds) the response slope of the reference electrode will be small. So long as the concentration of the redox reagent remains at a level so that the redox reagent is the potential determining species, there will be no electrode response to changing levels of electro-active contaminants in the test solution. The heterogeneous membrane formulated with a low electrolyte diffusion coefficient also impedes the transport of redox contaminants from the test solution to the electrode surface where they might compete as the potential determining reactants.

To better understand the design rules for formulating the heterogeneous salt bridge membrane according to this invention we present test data from a number of exemplar reference electrodes made in accordance with this invention and compare their electrical characteristics to computed simulation data.

In the simulations the time transient concentration of water diffusing in, reagents diffusing out and contaminants diffusing into the heterogeneous membrane's hydrophilic compartment was calculated using the previously described finite difference solution of the diffusion equations. A further refinement of the numerical simulation is the use of time and position variable salt diffusion coefficients in the membrane. This allows the modeling of membrane transport during the wet-up period, during which time the porosity and tortuosity (and thus the salt diffusion coefficients) of the hydrophilic path are changing. We have used the equation 1 relationship between membrane transport properties and water content.

REFERENCE ELECTRODE EXAMPLES

Reference electrodes were fabricated on commercially available smart-card modules. They comprised an epoxy foil body approximately 1 cm×1 cm and 0.01 cm in thickness with one side laminated with a 0.0015 cm copper which was plated with gold. The metal foil had been photo-formed into 8 contact pads in a geometry specified by the ISO standard for smart card modules. There were seven 0.8 mm diameter holes die-cut through the epoxy foil in regions above the contact metal.

The modules were used for preparation of electrodes as received from the vendor. The reference electrodes' heterogeneous membranes were printed by the pin-transfer printing technique. In this method a metal pin was immersed into the print solution to acquire a charge of print material. The pin with print material was then transferred to the surface of the module in the region of a passage through the epoxy. The print charge was deposited over the passage when the pin with its print material was brought into contact with the module surface. The wet thickness of the print was about 200–500 micrometers and the diameter about 1 mm to 1.2 mm. For testing purposes, we typically printed several electrodes per module with reference electrode membranes. Printed modules were air-dried for about 10 minutes at room temperature then on a hot-plate at about 70C. Membranes containing photo-cross-linkable PVA were then exposed to UV from a commercial dental lamp for 10 seconds. Modules were stored at room temperature (20–25C) and humidity (40–50% RH) prior to testing.

The print cocktail comprised an aqueous emulsion of siloxane with dissolved salts. The aqueous siloxane emulsion was SM2059 obtained from General Electric. This is a reactive amine terminated siloxane emulsion with cationic emulsifier. Weighed amounts of salts (and polyvinyl alcohol in some cocktails) were added to the as-received siloxane emulsion in amounts shown in the table below. The polyvinyl alcohol was a photo-cross-linkable formulation using stilbazonium functionalized polyvinyl alcohol (PVASBQ250 obtained from Esprix Technologies).

TABLE 2

| Print cocktail | Siloxane/PVA | PVA solids percent | siloxane solids percent | KCl milimole per gm siloxane | Potassium ferrocyanide micromole per gm siloxane | NaHEPES micromole per gm siloxane | HHEPES micromole per gm siloxane |
|---|---|---|---|---|---|---|---|
| PC020726-1B | SM2059/PVASBQ250 | 20% | 80% | 0.9 | 35 | 7.0 | 7.0 |
| PC020729-1 | SM2059/PVASBQ250 | 29% | 71% | 0.9 | 33 | 7.0 | 7.0 |

TABLE 2-continued

| Print cocktail | Siloxane/PVA | PVA solids percent | siloxane solids percent | KCl milimole per gm siloxane | Potassium ferrocyanide micromole per gm siloxane | NaHEPES micromole per gm siloxane | HHEPES micromole per gm siloxane |
|---|---|---|---|---|---|---|---|
| PC-020729-3 | SM2059/PVA18-88 | 41% | 59% | 0.9 | 50 | 10.0 | 10.0 |
| PC-020729-4 | SM2059/PVASBQ250 | 20% | 80% | 0.9 | 35 | 7.0 | 7.0 |
| PC-020729-4/1 | SM2059/PVASBQ250 | 11% | 89% | 0.5 | 18 | 3.5 | 35 |
| PC-020802-1 | SM2059/PVASBQ250 | 20% | 80% | 1.1 | 35 | 7.0 | 7.0 |
| PC-020802-1/1 | SM2059/PVASBQ250 | 10% | 90% | 0.9 | 18 | 3.5 | 3.5 |
| PC-020802-2 | SM2059 | | 100% | 1.1 | 35 | 7.0 | 7.0 |
| PC-021007-1 | SM2059 | | 100% | 1.19 | 35 | 7.0 | 7.0 |
| PC-021007-1/1 | SM2059 | | 100% | 0.3 | 8.7 | 1.7 | 1.7 |

Reference electrode membranes cured to a firm elastomer, whose dry thickness was in the range 50 to 200 micrometers.

Electrodes were tested in a fluidic cell. The cell comprised a fluidic chamber for introduction of aqueous fluids. The cell consisted of two spaced-apart planar surfaces, one being the electrode surface of the module for test, the other a slab of polycarbonate. The surfaces were spaced apart by a silicone rubber gasket which fluidically sealed the chamber. Fluids were introduced to the chamber through a first inlet pipe and removed through a second outlet pipe each connected through the polycarbonate slab. The contact surface of the module was contacted by a smart-card connector manufactured by Amphenol. There was a silver ground electrode in the inlet pipe and a commercial 3M KCl silver/silver chloride reference electrode (Microelectrodes Inc.) in the outlet pipe. For potentiometric measurements, each of the reference electrodes on the array of smart-card electrodes, and the in-line commercial reference electrode were connected to a high impedance source follower amplifier and then to a PC through a data acquisition card. For current-voltage measurements a voltage was applied to the in-line silver electrode and the smart-card electrodes were connected to current to voltage converters and then to a PC through a data acquisition card.

The test solutions were various HEPES buffered aqueous solutions containing sodium chloride and sodium bicarbonate

Example 1

Voltage Transients During Wet-Up

Figure 4:
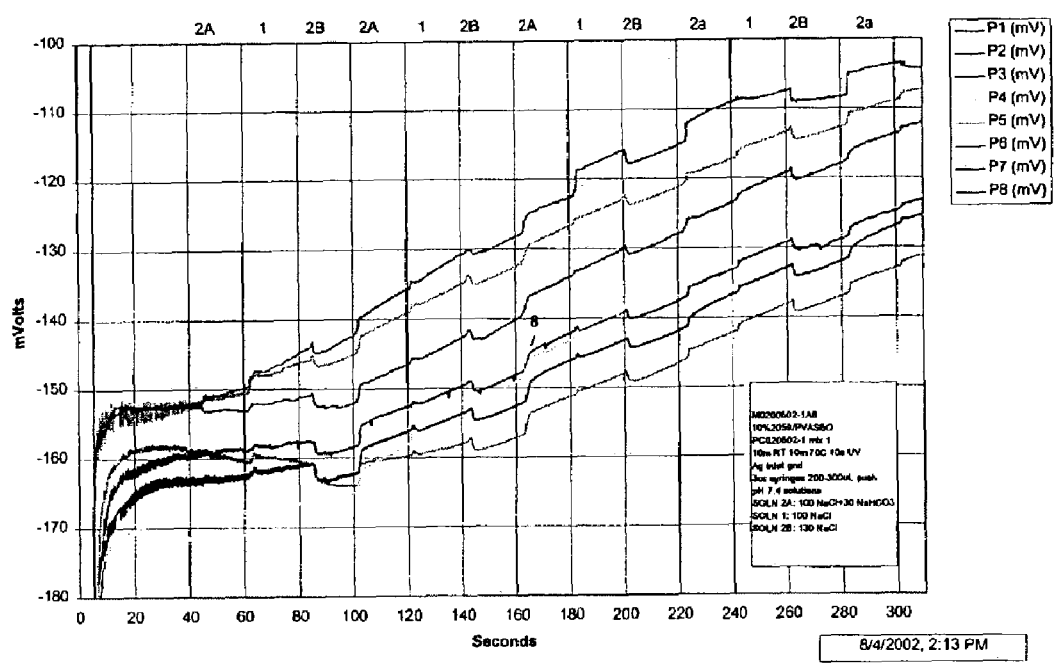
FIG. 4 is a graph of experimental electrode voltage data versus time of reference electrodes according to the invention.

The voltage versus time of a seven reference electrode array is shown in FIG. 4. This data is for an electrode array printed with formulation PC 020802-1/1 described in Table 2.

The data in this graph shows the signature voltage versus time transient of electrodes in accordance with this invention. There is a first rapid wet-up transient (0–30 secs) during which the electrode can be noisy and the voltage changes rapidly. This is followed by a plateau region in which the voltage changes more slowly and then a slow voltage change as salts leak out of the membrane.

We performed a simulation on a heterogeneous membrane with $V_H/V=0.01$, $V_E/V_H=0.06$ (giving $V_E/V=0.06\%$ for the membrane's equilibrium water content), $D_G=1\times10^{-5}$ cm$^2$ sec$^{-1}$, $S_G=1\times10^{-3}$ moles cm$^{-3}$ atm.$^{-1}$. The initial salt loading in the membrane's hydrophilic compartment was potassium chloride at $1\times10^{-2}$ moles cm$^{-3}$ and potassium ferrocyanide at $2\times10^{-3}$ moles cm$^{-3}$. The electrode voltage versus time was computed from the logarithm of the concentration of the potential determining ion (ferrocyanide) at the electrode surface.

The simulated salt concentration in the membrane at the electrode surface is shown in FIG. 5A, and the electrode voltage versus time in FIG. 5B. This simulation shows the same signature voltage transient as we observed experimentally. During the first 20 seconds there is an initial rapid decrease in potassium chloride and potassium ferrocyanide concentration because of water uptake. This is followed by a slower decrease by salt out-diffusion. The rate of decrease of the salt concentration increases with the salt diffusion coefficient which increases over time as the hydrophilic path acquires water according to equation 1. The terminal salt diffusion coefficient is computed from the above equation knowing the terminal water content of the hydrophilic path. The amount of salt out-diffusion for a given membrane increases as the membrane's salt diffusion coefficient. The amount of external contaminant (salt AB at 10 mM in the test solution) incorporated into the membrane also increases as the salt diffusion coefficient.

Example 2

Membrane Resistance Transients During Wet-Up

The data shown in FIG. 6A is the experimental membrane resistance versus time for an array of three electrodes with different thicknesses. These electrodes were printed with formulation PC021007-1 described in TABLE 2.

The experimental data of FIG. 6A also are signature transients of electrodes of this invention. There is a period (0–30 seconds for 100 micrometer thickness membrane, 0–90 seconds for 200 micrometer membranes) of wet-up during which the membrane resistance falls rapidly as water is acquired by the membrane's hydrophilic compartment. A minimum resistance corresponds to a membrane that has acquired equilibrium water and still retains the salts at substantially the amount initially loaded into the membrane. Over extended time the salts leak out and the membrane resistance increases again.

The membrane's bulk electrical resistance was simulated by computation of the transient salt concentration profiles and the wet-up time-dependent salt diffusion coefficients. This computation is shown in FIG. 6B. The simulation employed a water vapor diffusion coefficient of $1\times10^{-5}$ and a salt diffusion coefficient of $1\times10^{-7}$ cm$^2$ sec$^{-1}$. The simulation shows the same signature resistance transient as the experimental data.

The above data and the simulations show that during wet up until a time at which there is substantially complete water uptake the membrane's electrical resistance is large and quickly varying. Consequently, the reference electrode does not exhibit useful performance until after substantial wet up.

Example 3

Reference Electrode Performance

The potentiometric salt-bridge reference electrode of the current invention is directed to unit-use deployment with a single calibrator solution, primarily for in vitro blood analysis. In such an application the measurement time is typically less than 300 seconds.

The graph of FIG. 7 shows the experimental data on reference electrode responses of the liquid junction for a typical heterogeneous membrane formulated for application. The test data are the averaged responses taken from two modules each with seven reference electrodes. The heterogeneous membranes were printed using formulation PC-020802-2 from TABLE 2. In this formulation, the hydrophilic compartment comprises emulsifier and salts only, i.e there was no added polyvinyl alcohol binder. For the SM2059 series of formulations we found the best behavior at lowest PVA content with the optimum performance when there was no PVA binder.

In these tests, we introduced successively three different solutions into the flow cell. A first baseline solution 1 was 91 mM NaCl, 9 mM NaHepes and 11 mM HHepes, A second solution 2A (which was the baseline solution with 30 mM of chloride replaced by 30 mM bicarbonate) whose composition was 63 mM NaCl, 30 mM NaHCO$_3$, 7.5 mM NaHepes and 12.5 mM HHepes. A third solution 2B (which was the baseline solution with 30 mM additional NaCl) whose composition was 121 mM NaCl, 9 mM NaHepes, 11 mM HHepes. When the solution was changed from solution 1 to 2A or 2B the change in electrode potential relative to the commercial reference electrode was recorded, as well as the time that the change was made over a measurement period from complete wet-up to about 300 seconds.

The data shows that the reference electrode response generally increased with the time of immersion in test fluids, reaching +0.25 mV (30 mM bicarbonate addition) and −0.25 mV (30 mM chloride addition) at 300 seconds.

We also have performed simulations of the liquid junction response. We have used the finite difference diffusion model to calculate electrolyte concentrations versus time in the membrane. The potential difference between the electrolyte at the membrane's inner boundary and the electrolyte in the test solution at the membrane's outer boundary is the liquid junction potential which is calculated from Henderson's equation for liquid junctions using the electrolyte concentrations obtained from the numerical solutions of the diffusion equations. The Henderson equation, shown below, is well known in the art and described in many standard texts on the subject (for example A. J. Bard and L. R. Faulkner, Electrochemical Methods, John Wiley & Sons, 1980).

$$V = \frac{RT}{F} \frac{\sum_i \frac{\mu_i}{z_i}(C_i(L) - C_i(0))}{\sum_i \mu_i(C_i(L) - C_i(0))} LN \frac{\sum_i \mu_i C_i(L)}{\sum_i \mu_i C_i(0)} \quad \text{Equation 2}$$

The concentrations of all ions of type i in the aqueous compartment of the heterogeneous membrane are evaluated at the inner boundary $C_i(L)$ at the electrode surface and at the outer boundary in contact with the calibrator or test solution $C_i(0)$. $z_i$ and $\mu_i$ are the charge number and mobility of the i$^{th}$ ion respectively. This equation teaches that when there is a salt in the liquid junction at a dominant concentration and when the mobility of the salt's cations and the salt's anions are similar in value, the liquid junction potential will be small and independent of all other salt concentrations in the junction. Therefore, the industry standard salt-bridge reference electrode uses a salt bridge composed of 3 or 4M potassium chloride whose ions are approximately equi-mobile at a concentration which is close to the saturation solubility. The calculation of the liquid junction potential of the invented heterogeneous membrane uses values of ion mobility in the membrane obtained from the mobility within the membrane's aqueous capillary pores (typically same as in a pure aqueous electrolyte) multiplied by the tortuosity factor. In a good liquid junction it is necessary that there are no specific interactions between the diffusing ion and components of the hydrophilic compartment. Such interactions manifest themselves as changes in the relative mobilities of ions from their values in a pure aqueous electrolyte. For a membrane to be an effective salt bridge matrix exhibiting a small liquid junction potential, the relative mobility of potassium and chloride ions should be approximately the same as in the pure aqueous electrolyte, that is to say they should be about equi-mobile.

In the simulation, the liquid junction potential is calculated when the device is first immersed in solution 1, then immersed in a second test solution 2A or 2B with a different composition. The potential difference from solution 1 to 2 represents the liquid junction response. The graph of FIG. 7 plots the calculated change of liquid-junction potential in milivolts (DmV y-axis) versus time. As with the experimental data, the calculation also shows an increase in liquid junction potential versus time and is in concordance with the gradual decrease over time of the potassium chloride concentration within the membrane.

The data and the simulation quantify the change of liquid-junction potential when the composition of the dominant electrolyte ions in the test solution (sodium, chloride and bicarbonate when the test solution is blood) are changed by 30 ml/L around a mid point composition close to the composition of normal blood. A change of 30 mM represents the 99% range of blood compositions of these ions around the normal blood composition. This change represents the maximum compositional range over which the reference electrode's liquid junction response should remain within a specified limit. When using a potentiometric indicator electrode in combination with a salt-bridge reference electrode in the measurement of a univalent ion concentration, an error in the measurement of +/−1% is incurred for every −/+0.25 mV of the reference electrode's liquid junction error. To achieve less than a specified 2% measurement error (typically required for the in-vitro blood analysis application), the reference electrode's liquid junction should contribute no more than +/−0.5 mV of response.

The data shows that the exemplar reference electrodes can be used to 300 seconds and contribute less than +/−0.25 mV error. The corresponding simulation teaches a threshold for the depleted concentration of the salt-bridge potassium chloride of 0.6 mol/L at the point of measurement to achieve an error of less than 0.25 mV relative to the response of the industry standard reference electrode with a 3 or 4 M potassium chloride liquid junction. To achieve less than 1% error relative to the industry standard reference electrode the liquid junction should contribute no more than 0.25 mV. The threshold concentration of potassium chloride at 1% tolerance is about 1M.

Other exemplar reference electrodes, for example ones with formulation PC-020802-1/1 show a larger reference response of +/−0.5 mV at 100 seconds rising to +/−1 mV after 200 seconds. These electrodes exceed the 2% tolerance limit after 100 seconds and the measurement must be performed earlier than 100 seconds to achieve the desired 2% tolerance. The simulation shows results consistent with more rapid salt depletion at a diffusion coefficient of 3–5× $10^{-7}$ $cm^2$ $sec^{-1}$.

The design rule to determine the optimal time window in which to perform a potentiometric measurement can be now summarized as the time between which the membrane has substantially wet-up and the time at which the membrane's potassium chloride has depleted to 1M (1% tolerance) to 0.6M (2% tolerance). This time window will depend on the relative diffusion coefficients of water transport into and salt transport out of the membrane.

The rate of diffusive influx and efflux of material from the membrane can be approximately understood in terms of characteristic times. The characteristic time $t_c$ for a diffusive process scales with the thickness squared divided by the diffusion coefficient: $t_c \sim L^2/D$. For water influx into a 0.01 cm thickness membrane at $D=1\times10^{-5}$ $cm^2$ $sec^{-1}$, $t_c=10$ seconds and the time to 95% completion is about $-LN(0.05)$ $t_c=30$ seconds. For salt efflux from a 0.01 cm thickness membrane at $D=1\times10^{-7}$ $cm^2$ $sec^{-1}$, $t_c=1000$ seconds and the time to say 50% depletion is about $-LN(0.5)tc=690$ seconds. For salt efflux from a 0.01 cm thickness membrane at $D=5\times10^{-7}$ $cm^2$ $sec^{-1}$, $t_c=200$ seconds, and the time to 50% depletion is about $-LN(0.5)t_c=138$ seconds. For salt efflux from a 0.01 cm thickness membrane at $D=1\times10^{-6}$ $cm^2$ $sec^{-1}$, $t_c=100$ seconds, and the time to 50% depletion is about $-LN(0.5)t_c=69$ seconds.

The heterogeneous membrane of the salt bridge reference electrode of this invention is marginally useful when the ratio of water and salt diffusion is only about 10. If the nominal measurement time is established at 44 seconds for a nominal 0.01 cm thickness membrane the measurement time falls outside of the window when the membrane thickness is instead 0.008 cm thick (nominal thickness minus 20%) or 0.012 cm (nominal thickness plus 20%). Membranes should be printed at nominal thickness +/−20%/ 3=7% coefficient of variation to be consistently within specification. Such a membrane composition is thus not robust to variations in the membrane thickness. When the ration of water to salt diffusion coefficient is 20, the required membrane thickness specification is nominal +/−36%/ 3=12% CV. When the ratio is 100 the required membrane thickness specification is nominal +/−65%/3=22% CV. These membranes are robust to variations in membrane thickness.

We have preferred to fabricate salt bridge reference electrodes with a single heterogeneous membrane coating step on a metal electrode. As shown above this requires the heterogeneous membrane to provide the internal salt reservoir containing potassium chloride and redox reagent within its hydrophilic compartment. It is clearly also feasible to make reference electrodes which are still significantly simpler to produce than prior-art devices, but include two membranes coating the metal electrode. The first is an internal reservoir layer comprising a hydrophilic compartment containing the reservoir salts. The second is a heterogeneous membrane which has a water vapor permeable compartment and a hydrophilic compartment. The heterogeneous membrane's water vapor permeable compartment permits water vapor transport to allow wet-up of both the internal hydrophilic layer and the heterogeneous membrane's hydrophilic compartment. The heterogeneous membrane's hydrophilic compartment permits transport of salts between the internal reservoir and the test solution to establish the liquid junction.

Diagnostic Cards using Electrodes of this Invention

The electrodes of this invention are uniquely suitable for deployment in unit-use diagnostic devices with a single calibrator solution. A unit-use diagnostic card has been configured in a single integral unit we call a diagnostic test card. Diagnostic test cards with sensors and integral calibrators are well known in the art. However, heretofore none have been made in as cost-effective manner as described here. We have disclosed cost-effective diagnostic cards incorporating electrode modules in co-pending application U.S. Ser. No. 09/871,823. We describe herein in more detail a diagnostic card formatted for use with electrode modules and heterogeneous membrane electrodes of this invention. The new card represents a far more cost-effective, integrated measurement device than any device of the current art.

Figure 8A:
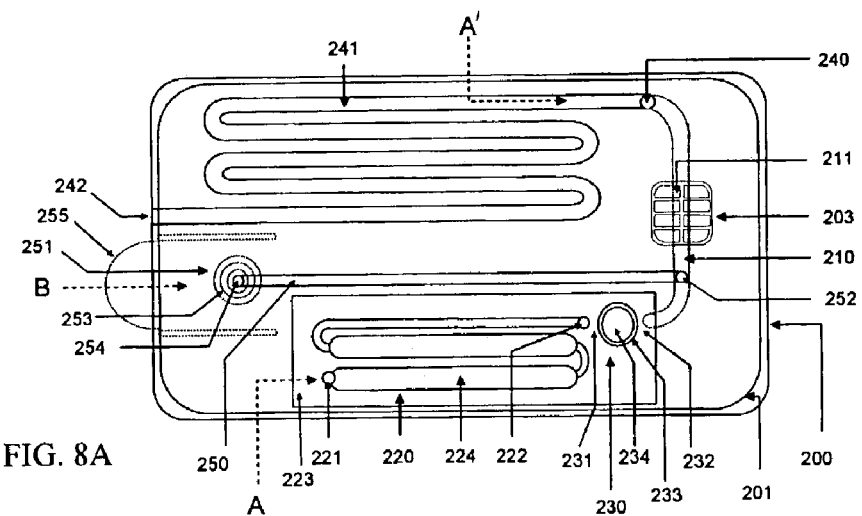
FIG. 8A is a lower surface schematic view of a diagnostic card with integral fluidics and including electrodes according to this invention.
Figure 8B:
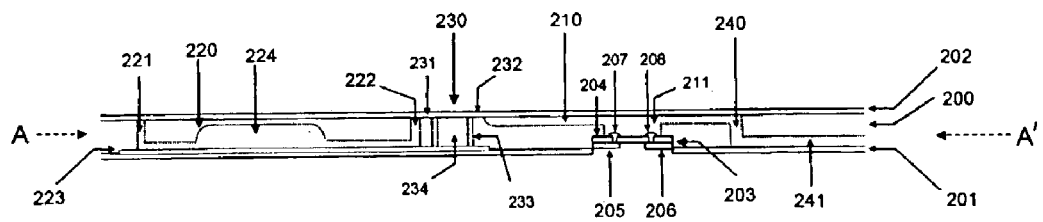
FIG. 8B is a side-view schematic of the diagnostic card of FIG. 8A along the fluidic path AA'.
Figure 8C:
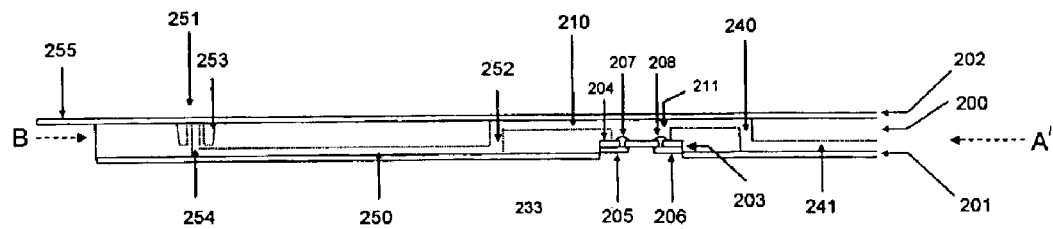
FIG. 8C is a side-view schematic of the diagnostic card of FIG. 8A along the fluidic path BA'.

FIGS. 8A–8C shows a bottom plan view and two cross-sectional view schematics of a diagnostic card including an electrode module with heterogeneous membrane electrodes in accordance with the invention. The schematic cross-section AA' of FIG. 8B is along the fluidic path from a calibrator chamber 220 through the measurement cell 211 to a waste channel 241, and the other schematic cross-section $B^{4'}$ of FIG. 8C is along a fluidic path from the sample entry port 251 through the measurement cell 211 to a waste channel 241.

Referring to FIGS. 8A–8C, the diagnostic card in the preferred embodiment is a credit-card sized molded plastic housing 200 with an electrode module 203 embedded in the lower surface of the housing. The electrode module is an array of electrodes comprising heterogeneous membranes of this invention. It has an epoxy foil element 204 with die-cut throughgoing passages laminated with a gold plated copper foil that has been photo-formed into eight electrode contact elements. Two contact elements 205 and 206 are shown in the side-view schematic diagrams. Heterogeneous membranes 207 and 208 are shown contacting metal contacts 205 and 206 through the passages in the epoxy on the top surface of the module. Preferably, the dimensions of the electrode module and its contact metals conform to ISO specifications established for electronic smart cards. The housing 200 also contains molded features (grooves, trenches and holes) on both its upper (dotted lines in the bottom view schematic) and lower (solid lines in the bottom view schematic) surfaces which, when sealed, form fluidic channels and a sealed fluid reservoir. Seals are made to the lower and upper surface of the housing by lamination with seal elements 201 and 202 and 223. Seal element 201 on the lower surface of the card is a die-cut adhesive coated polymer sheet. Seal element 202 on the upper surface is also a die-cut adhesive coated sheet, chosen to be gas impermeable, somewhat mechanically rigid and transparent or semi-transparent. Element 203 is a die-cut metal foil coated with poly-vinylidene chloride for heat sealing.

There are two trenches on the lower surface of the plastic housing. When sealed by element 223 they form a chamber 220 with a volume of about 150 micro-liters. A fill port 221 extends through the plastic housing 200 through which a calibrator solution 224 can be injected from the upper surface of the housing to fill the chamber 220, with a vent port 222, also through the housing, providing for the venting of air from the chamber 220 during the filling process. The chamber filled with fluid is completely sealed when the ports 221 and 222 are closed-off by seal element 202 laminated to the upper surface of the housing.

There is a fluidic channel 210 connecting the calibrator chamber to the measurement cell 211 above the module and then to a waste channel 241. A second fluidic channel 250 connects a sample inlet port 251 to the measurement cell. A breakable seal 230 is provided in the channel between the measurement cell and the calibrator chamber for selective opening of the calibrator chamber. This seal 230 includes a plug 234 fitted into an aperture 233 through the housing 200 to permit sliding displacement of the plug within the housing aperture. As will be described in more detail below, regions 231 and 232 of the seal between housing 200 and seal element 202 in the vicinity of plug 234 are de-laminated upon upwards movement of the plug 234.

The card is assembled as follows. The molded plastic housing 200 as received is first laminated with the electrode module 203 and calibrator chamber seal element 223. Calibrator fluid is injected through port 221 into chamber 220. Heterogeneous membranes can be printed onto the module at this point in the assembly process or they can also be printed prior to assembly of the module. Lamination of the card housing with upper seal element 202 then lower seal element 201 completes the process. The upper seal element 202 includes a flap portion 290 which allows partial lifting of the seal element from the housing 200.

Figure 9A:
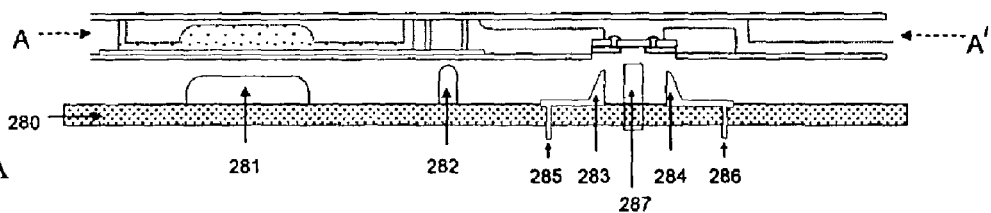
FIG. 9A is a side view schematic of the diagnostic card along fluidic path AA' and the card reader's mating elements in the initial position.

In use, the card is inserted into a card reader device comprising a planar mating element 280 with various features as shown schematically in FIG. 9A.

Figure 9B:
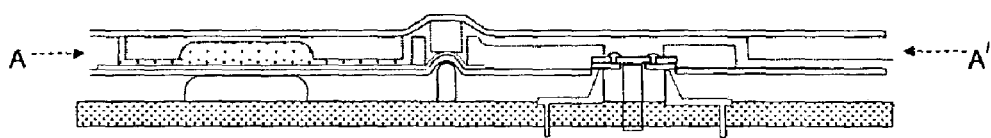
FIG. 9B is a side view schematic of the diagnostic card along fluidic path AA' and the card reader's mating elements as the card is lowered onto the mating surface.
Figure 9C:
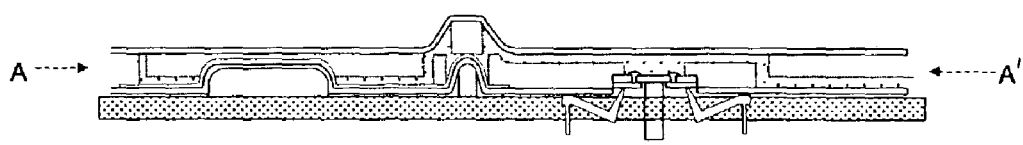
FIG. 9C is a side view schematic of the diagnostic card along fluidic path AA' and the card reader's mating elements when the card has fully contacted the mating surface.
Figure 10:
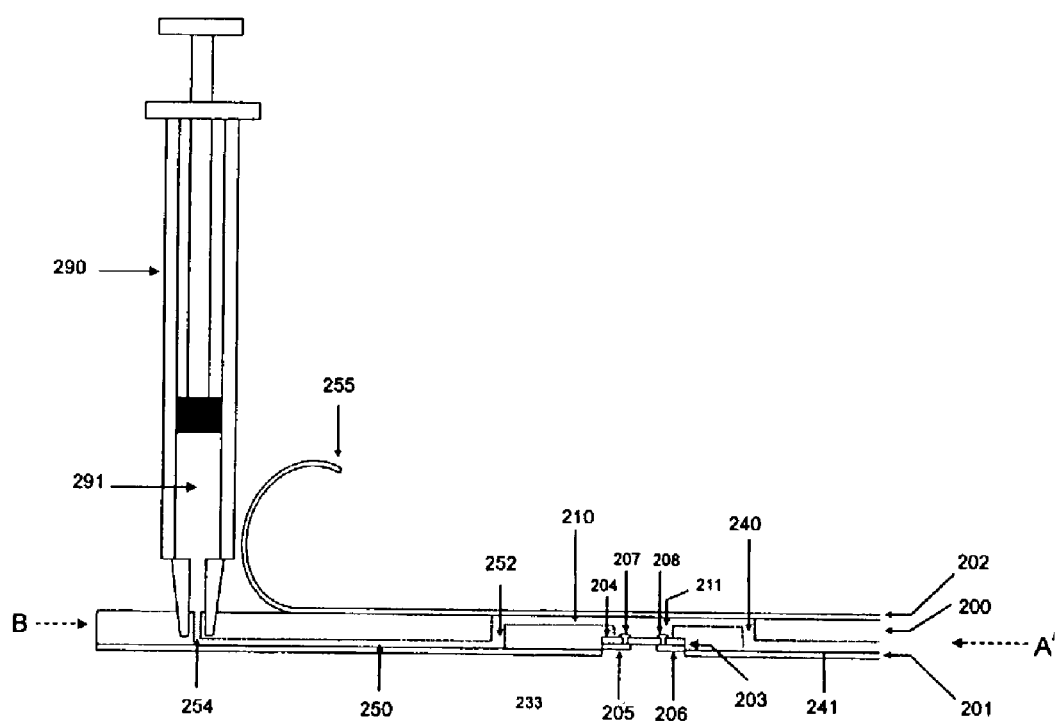
FIG. 10 is a side view schematic of the diagnostic card along fluidic path BA' and sample delivery from a syringe.

The card reader's card insertion orifice has a guide for aligning the features on the card with their respective mating features on the card reader's mating element. The lower surface of the card is brought into contact with the mating surface of the card reader. As the card is brought into contact with the mating surface, the pin element 282 first contacts the card at the calibrator chamber outlet valve 230 (FIG. 9B). The pin pushes plug 234 upwards. This lifts the semi-rigid laminate 202 causing de-lamination at seal points 231 and 232, thus fluidically opening the calibrator chamber. At the same time the electrode module is contacted by an electrode module contacting arrangement including an array of eight contact pins also embedded in the mating surface of the card reader. Two of the eight pins are shown in the side view schematic of FIG. 9A. Each has a contact end 283, 284 for making z-action contact to the contact elements 205, 206 on the lower surface of the electrode module, and an end 285, 286 for contact to an electrical circuit measurement arrangement. At the same time, the electrode module is also contacted by a heater block 287. The heater block 287 makes thermal contact with the module on its lower surface directly under the measurement chamber. The heater block contains a heater element and a temperature measuring element each in intimate thermal contact with the block. Heater element and temperature measuring element are also connected to the electrical circuit. As the card continues to be lowered over the mating surface, the pin element 281 now engages the calibrator chamber 220 and compresses it causing delivery of fluid out of the chamber along fluidic channel 210 to measurement chamber 211 (FIG. 9C). After a calibration period, the card-reader prompts the user to supply sample fluid to the diagnostic card. The user lifts flap 290 thereby detaching the seal element 202 from the housing 200 in the region of the sample port 251 and then engages a syringe containing sample to the luer-type fitting in the card's sample entry port 251. The user delivers sample from the syringe to the measurement cell 211 along channel 250, thus displacing calibrator fluid out of chamber 211 to waste chamber 241. This is shown schematically in FIG. 10. The sample injection step is continued until substantially all of the calibrator fluid is forced from the measurement cell 211, which can be visually confirmed due to the transparent properties of the seal element 201, at least in the area above the measurement cell. Measurement of the sample is carried out immediately after completion of the sample injection.

Although specific embodiments of the invention have been described herein for purposes of illustration, various modifications may be made without deviating from the spirit and scope thereof.

What is claimed is:

1. A potentiometric reference electrode for use in an electrochemical analysis of an aqueous sample, comprising
    an electric conductor;
    an insulating layer on the conductor, the insulating layer having a throughgoing aperture defining an electrode region; and
    a heterogeneous membrane layer on the insulating layer in the electrode region for direct contact with the sample and for electrical contact with the conductor through the aperture, the heterogeneous membrane layer having at least one hydrophobic, gas permeable compartment having a water vapor diffusion coefficient and at least one hydrophilic, ion conducting electrolyte compartment having an aqueous electrolyte diffusion coefficient lower than the water vapor diffusion coefficient of the hydrophobic compartment.

2. The electrode as defined in claim 1, wherein the heterogeneous membrane includes a plurality of hydrophobic and hydrophilic compartments which are intimately admixed.

3. The electrode as defined in claim 2, wherein the water vapor diffusion coefficient is at least 50 times higher then the aqueous electrolyte diffusion coefficient.

4. The electrode as defined in claim 2, wherein the water vapor diffusion coefficient is at least $5 \times 10^{-6}$ cm$^2$ sec$^{-1}$ and the aqueous electrolyte diffusion coefficient is at most $5 \times 10^{-7}$ cm$^2$ sec$^{-1}$.

5. The electrode as defined in claim 1, wherein the conductor is one of an array of n metallic conductors, and the insulating layer has n throughgoing apertures, each defining an electrode region and being located over one of the metallic conductors.

6. The electrode as defined in claim 5, wherein the heterogeneous membrane layer is one of n membrane layers respectively contacting one of the n metallic conductors.

7. The electrode as defined in claim 1, wherein the relative amounts of the hydrophilic and hydrophobic compartments vary within the membrane.

8. The electrode as defined in claim 1, wherein the heterogeneous membrane is constructed of a material which has a substantially dry, inactive condition and a wet-up active condition and permits diffusion of water vapor through the hydrophobic compartment for conversion from the inactive condition to the active condition.

9. The electrode as defined in claim 8, wherein the hydrophilic compartment of the membrane includes reagent and is constructed to permit, in the active condition and upon exposure to the aqueous sample fluid, a diffusion of the reagents from the membrane layer into the sample fluid.

10. The electrode as defined in claim 8, wherein the membrane in the active condition further permits diffusion of contaminants into the membrane layer.

11. The electrode of claim 1, wherein the conductor is a layer of copper coated with gold.

12. The electrode of claim 1, wherein the insulator is a layer of epoxy or filled epoxy.

13. The electrode of claim 12, wherein the throughgoing aperture is drilled or die-cut in the epoxy insulator.

14. The electrode of claim 1, wherein the hydrophobic compartment of the heterogeneous membrane comprises a polymer selected from the group of poly-siloxanes, poly-organo-phosphazenes, poly-1trimethyl-silyl-1-propyne, poly-4-methyl-2-pentyne and mixtures thereof.

15. The electrode of claim 1, wherein the heterogeneous membrane material is an emulsion in dried form.

16. The electrode of claim 15, wherein the emulsion is a siloxane in water emulsion and the water contains dissolved salts.

17. The electrode of claim 1, wherein the hydrophilic compartment contains electrolyte salts.

18. The electrode of claim 17, wherein the salt comprises equi-mobile ions.

19. The electrode of claim 17, wherein the hydrophilic compartment contains a redox reagent for undergoing a potential determining reaction at the electrode.

20. The electrode of claim 17, wherein the hydrophilic compartment contains salts with equi-mobile ions and a potential determining redox reagent.

21. The electrode of claim 18 or 20, wherein the salt with equi-mobile ions is potassium chloride.

22. The electrode of claim 19 or 20, wherein the redox reagent is ferrocyanide.

23. The electrode as defined in claim 19 or 20, wherein the hydrophilic compartment further includes at least one of a hydrophilic polymeric binder, a surfactant, an emulsifier and a pH buffer.

24. The electrode as defined in claim 23, wherein the hydrophilic polymeric binder is polyvinyl alcohol.

25. The electrode as defined in claim 1, wherein the water vapor diffusion coefficient Is at least 10 times higher then the aqueous electrolyte diffusion coefficient.

26. A process for the manufacture of an electrode as defined in claim 1, including the step of casting the heterogeneous membrane from a volatilizable fluid.

27. The process as defined in claim 26, wherein the heterogeneous membrane layer is cast by a method selected from the group of printing by dispensing through a nozzle, pin-transfer printing, spin-coating, dip-coating, screen-printing and stencil printing.

28. A salt-bridge reference electrode for use in electrochemical analysis of an aqueous sample, comprising
a metal conductor;
a heterogeneous membrane for contact with the sample, the membrane being located on the conductor for electric contact therewith and including a water vapor permeable hydrophobic compartment and a hydrophilic compartment containing a salt component of ions of approximately equal ionic mobilities and a redox component for undergoing a potential determining reaction at the metal conductor, the hydrophilic compartment having an aqueous electrolyte diffusion coefficient lower than the water vapor diffusion coefficient of the hydrophobic compartment.

29. The electrode as defined in claim 28, wherein the heterogeneous membrane layer has at least one hydrophobic, gas permeable compartment and at least one hydrophilic, ion conducting electrolyte compartment.

30. A salt-bridge reference electrode as defined in claim 28, wherein the heterogeneous membrane has a substantially dry, inactive condition and a wet-up, active condition and is convertible from the inactive condition to the active condition by water vapor transport through the hydrophobic compartment, the membrane being constructed for permitting, in the active condition and upon exposure to the aqueous sample fluid, diffusion of at least one soluble component of the membrane layer into the sample fluid.

31. Use of an electrode as defined in claim 30, comprising the steps of exposing the electrode to water for converting the membrane layer from the dry, inactive condition to the wet-up, active condition, exposing the membrane layer to the sample fluid, and measuring an electric potential at the conductor while the concentration of the salt in the electrolyte phase decreases, due to diffusion thereof into the sample fluid, but is still above a pre-selected threshold concentration at which the response slope of the reference electrode exceeds a pre-selected value.

32. The use as defined in claim 31, wherein the step of measuring is carried out while a concentration of the redox component in the membrane layer decreases, due to diffusion thereof into the sample fluid and diffusion of contaminants from the sample fluid into the membrane layer, but only while the redox component remains the potential determining species.

33. The electrode as defined in claim 28, wherein the water vapor diffusion coefficient is at least 10 times higher then the aqueous electrolyte diffusion coefficient.

34. The electrode as defined in claim 33, wherein the water vapor diffusion coefficient is at least 50 times higher then the aqueous electrolyte diffusion coefficient.

35. The electrode as defined in claim 33, wherein the water vapor diffusion coefficient is at least $5 \times 10^{-6}$ cm$^2$ sec$^{-1}$ and the aqueous electrolyte diffusion coefficient is at most $5 \times 10^{-7}$ cm$^2$ sec$^{-1}$.

36. A salt bridge reference electrode, wherein the salt bridge comprises a heterogeneous membrane with a hydrophobic water vapor permeable compartment and a hydrophilic ion conducting electrolyte compartment containing salts, the hydrophobic compartment having a water vapor diffusion coefficient and the hydrophilic compartment having an aqueous electrolyte diffusion coefficient lower than the water vapor diffusion coefficient of the hydrophobic compartment.

37. A salt bridge reference electrode as defined in claim 36, wherein the membrane is in electric contact with a conductor.

38. The electrode as defined in claim 36, wherein the water vapor diffusion coefficient is at least 10 times higher then the aqueous electrolyte diffusion coefficient.

39. The electrode as defined in claim 38, wherein the water vapor diffusion coefficient is at least 50 times higher then the aqueous electrolyte diffusion coefficient.

40. The electrode as defined in claim 38, wherein the water vapor diffusion coefficient is at least $5 \times 10^{-6}$ cm$^2$ sec$^{-1}$ and the aqueous electrolyte diffusion coefficient is at most $5 \times 10^{-7}$ cm$^2$ sec$^{-1}$.

41. The electrode as defined in claim 36, wherein the water vapor diffusion coefficient is at least 10 times higher then the aqueous electrolyte diffusion coefficient.

42. The electrode as defined in claim 41, wherein the water vapor diffusion coefficient is at least 50 times higher then the aqueous electrolyte diffusion coefficient.

43. The electrode as defined in claim 41, wherein the water vapor diffusion coefficient is at least $5 \times 10^{-6}$ cm$^2$ sec$^{-1}$ and the aqueous electrolyte diffusion coefficient is at most $5 \times 10^{-7}$ cm$^2$ sec$^{-1}$.

* * * * *

UNITED STATES PATENT AND TRADEMARK OFFICE
CERTIFICATE OF CORRECTION

PATENT NO. : 7,094,330 B2 Page 1 of 1
APPLICATION NO. : 10/307481
DATED : August 22, 2006
INVENTOR(S) : Imants Lauks et al.

It is certified that error appears in the above-identified patent and that said Letters Patent is hereby corrected as shown below:

Column 26, line 48 (claim 6) delete "claim 5" and insert therefor --claim 1--;

Column 27, line 37 (claim 25), delete "Is" and insert therefor --is--;

Column 27, line 37 (claim 25), delete "then" and insert therefor -- than --;

Column 28, line 56 (claim 41), delete "claim 36" and insert therefor -- claim 37 --.

Signed and Sealed this

Thirteenth Day of March, 2007

JON W. DUDAS
*Director of the United States Patent and Trademark Office*